United States Patent
Decker et al.

(10) Patent No.: US 11,357,504 B2
(45) Date of Patent: Jun. 14, 2022

(54) SURGICAL STAPLER HAVING LOCKING ARTICULATION JOINT

(71) Applicant: Applied Medical Resources Corporation, Rancho Santa Margarita, CA (US)

(72) Inventors: Steven E. Decker, Anaheim, CA (US); Atal C. Patel, Mission Viejo, CA (US); Erik D. Nelson, Santa Clara, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 271 days.

(21) Appl. No.: 16/657,086

(22) Filed: Oct. 18, 2019

(65) Prior Publication Data

US 2020/0046354 A1    Feb. 13, 2020

Related U.S. Application Data

(63) Continuation of application No. 15/230,833, filed on Aug. 8, 2016, now Pat. No. 10,448,949.

(60) Provisional application No. 62/201,995, filed on Aug. 6, 2015.

(51) Int. Cl.
| | |
|---|---|
| *A61B 17/064* | (2006.01) |
| *A61B 17/072* | (2006.01) |
| *A61B 17/29* | (2006.01) |

(52) U.S. Cl.
CPC ............. *A61B 17/07207* (2013.01); *A61B 2017/2927* (2013.01)

(58) Field of Classification Search
CPC ...... A61B 2017/003; A61B 2017/2926; A61B 2017/2927; A61B 2017/2946
See application file for complete search history.

(56) References Cited

U.S. PATENT DOCUMENTS

| | | |
|---|---|---|
| 2,073,960 A | 3/1937 | Crosby |
| 2,140,593 A | 12/1938 | Pankonin |
| 2,351,608 A | 6/1944 | Greenwood |

(Continued)

FOREIGN PATENT DOCUMENTS

| | | |
|---|---|---|
| EP | 0 251 444 A1 | 1/1988 |
| EP | 0 492 283 A1 | 7/1992 |

(Continued)

OTHER PUBLICATIONS

The International Bureau of WIPO, International Preliminary Report on Patentability, for International Application No. PCT/US2019/019867, entitled "Surgical Stapler Having a Powered Handle," dated Sep. 3, 2020, 16 pgs.

(Continued)

*Primary Examiner* — Eyamindae C Jallow
(74) *Attorney, Agent, or Firm* — John F. Heal

(57) ABSTRACT

A laparoscopic surgical stapler can include an articulation joint between an elongate shaft and a jaw assembly. The articulation joint can include a latch mechanism allowing a user to selectively allow the jaw assembly to be freely pivotable with respect to the elongate shaft in an unlatched configuration and positionable in an aligned position or one of several predetermined articulated positions in a latched configuration. The latch mechanism of the articulation joint is biased to the latched configuration and is operable in a 'push-to-release' manner.

20 Claims, 6 Drawing Sheets

(56) References Cited

U.S. PATENT DOCUMENTS

| | | |
|---|---|---|
| 2,487,565 A | 11/1949 | Leber et al. |
| 2,641,154 A | 6/1953 | Heller |
| 3,076,373 A | 2/1963 | Matthews |
| 3,077,812 A | 2/1963 | Dietrich |
| 3,080,564 A | 3/1963 | Strekopitov et al. |
| 3,203,220 A | 8/1965 | Kaepernik |
| 3,252,643 A | 5/1966 | Strekopitov et al. |
| 3,273,562 A | 9/1966 | Brown |
| 3,373,646 A | 3/1968 | Ehlert |
| 3,459,187 A | 8/1969 | Pallotta |
| 3,494,533 A | 2/1970 | Green et al. |
| 3,662,939 A | 5/1972 | Bryan |
| 3,675,688 A | 7/1972 | Bryan et al. |
| 3,692,224 A | 9/1972 | Astafiev et al. |
| 4,261,244 A | 4/1981 | Becht et al. |
| 4,281,785 A | 8/1981 | Brooks |
| 4,304,236 A | 12/1981 | Conta et al. |
| 4,312,363 A | 1/1982 | Rothfuss et al. |
| 4,317,451 A | 3/1982 | Cerwin et al. |
| 4,407,286 A | 10/1983 | Noiles et al. |
| 4,434,796 A | 3/1984 | Karapetian et al. |
| 4,442,964 A | 4/1984 | Becht |
| 4,454,875 A | 6/1984 | Pratt et al. |
| 4,522,327 A | 6/1985 | Korthoff et al. |
| 4,527,724 A | 7/1985 | Chow et al. |
| 4,589,582 A | 5/1986 | Bilotti |
| 4,591,085 A | 5/1986 | Di Giovanni |
| 4,606,344 A | 8/1986 | Di Giovanni |
| 4,608,981 A | 9/1986 | Rothfuss et al. |
| 4,610,383 A | 9/1986 | Rothfuss et al. |
| 4,728,020 A | 3/1988 | Green et al. |
| 4,805,823 A | 2/1989 | Rothfuss |
| 4,892,244 A | 1/1990 | Fox et al. |
| 4,923,350 A | 5/1990 | Hinksman et al. |
| 4,941,623 A | 7/1990 | Pruitt |
| 4,955,959 A | 9/1990 | Tompkins et al. |
| 4,978,049 A | 12/1990 | Green |
| 5,031,814 A | 7/1991 | Tompkins et al. |
| 5,065,929 A | 11/1991 | Schulze et al. |
| 5,071,052 A | 12/1991 | Rodak et al. |
| 5,106,008 A | 4/1992 | Tompkins et al. |
| 5,116,349 A | 5/1992 | Aranyi |
| 5,129,570 A | 7/1992 | Schulze et al. |
| 5,201,746 A | 4/1993 | Shichman |
| 5,221,036 A | 6/1993 | Takase |
| 5,236,440 A | 8/1993 | Hlavacek |
| 5,240,163 A | 8/1993 | Stein et al. |
| RE34,519 E | 1/1994 | Fox et al. |
| 5,275,323 A | 1/1994 | Schulze et al. |
| 5,289,963 A | 3/1994 | McGarry et al. |
| D347,474 S | 5/1994 | Olson |
| 5,307,976 A | 5/1994 | Olson et al. |
| 5,308,576 A | 5/1994 | Green et al. |
| 5,326,013 A | 7/1994 | Green et al. |
| 5,350,400 A | 9/1994 | Esposito et al. |
| 5,360,305 A | 11/1994 | Kerrigan |
| 5,364,002 A | 11/1994 | Green et al. |
| 5,366,479 A | 11/1994 | McGarry et al. |
| 5,381,943 A | 1/1995 | Allen et al. |
| 5,389,098 A | 2/1995 | Tsuruta et al. |
| 5,395,034 A | 3/1995 | Allen et al. |
| 5,397,046 A | 3/1995 | Savage et al. |
| 5,413,267 A | 5/1995 | Solyntjes et al. |
| 5,415,334 A | 5/1995 | Williamson, IV et al. |
| 5,415,335 A | 5/1995 | Knodell, Jr. |
| 5,439,155 A | 8/1995 | Viola |
| 5,439,479 A | 8/1995 | Shichman et al. |
| 5,445,304 A | 8/1995 | Plyley et al. |
| 5,447,265 A | 9/1995 | Vidal et al. |
| 5,452,836 A | 9/1995 | Huitema et al. |
| 5,456,401 A | 10/1995 | Green et al. |
| 5,458,279 A | 10/1995 | Plyley |
| 5,462,215 A | 10/1995 | Viola et al. |
| 5,464,144 A | 11/1995 | Guy et al. |
| 5,465,895 A | 11/1995 | Knodel et al. |
| 5,470,006 A | 11/1995 | Rodak |
| 5,470,007 A | 11/1995 | Plyley et al. |
| 5,470,008 A | 11/1995 | Rodak |
| 5,470,009 A | 11/1995 | Rodak |
| 5,472,132 A | 12/1995 | Savage et al. |
| 5,480,089 A | 1/1996 | Blewett |
| 5,485,952 A | 1/1996 | Fontayne |
| 5,487,500 A | 1/1996 | Knodel et al. |
| 5,489,058 A | 2/1996 | Plyley |
| 5,497,933 A | 3/1996 | DeFonzo et al. |
| 5,507,426 A | 4/1996 | Young et al. |
| 5,507,773 A | 4/1996 | Huitema et al. |
| 5,509,596 A | 4/1996 | Green et al. |
| 5,509,920 A | 4/1996 | Phillips et al. |
| 5,529,235 A | 6/1996 | Boiarski et al. |
| 5,547,117 A | 8/1996 | Hamblin et al. |
| 5,553,765 A | 9/1996 | Knodel et al. |
| 5,554,164 A | 9/1996 | Wilson et al. |
| 5,558,266 A | 9/1996 | Green et al. |
| 5,562,241 A | 10/1996 | Knodel et al. |
| 5,562,700 A | 10/1996 | Huitema et al. |
| 5,562,701 A | 10/1996 | Huitema et al. |
| 5,562,702 A | 10/1996 | Huitema et al. |
| 5,564,615 A | 10/1996 | Bishop et al. |
| 5,571,285 A | 11/1996 | Chow et al. |
| 5,579,978 A | 12/1996 | Green et al. |
| 5,580,067 A | 12/1996 | Hamblin et al. |
| 5,584,425 A | 12/1996 | Savage et al. |
| 5,586,711 A | 12/1996 | Plyley et al. |
| 5,588,581 A | 12/1996 | Conlon et al. |
| 5,597,107 A | 1/1997 | Knodel et al. |
| 5,601,224 A | 2/1997 | Bishop et al. |
| 5,605,272 A | 2/1997 | Witt et al. |
| 5,607,095 A | 3/1997 | Smith et al. |
| 5,615,820 A | 4/1997 | Viola |
| 5,626,587 A | 5/1997 | Bishop et al. |
| 5,630,539 A | 5/1997 | Plyley et al. |
| 5,634,584 A | 6/1997 | Okorocha et al. |
| 5,636,779 A | 6/1997 | Palmer |
| 5,657,921 A | 8/1997 | Young et al. |
| 5,662,258 A | 9/1997 | Knodel et al. |
| 5,662,662 A | 9/1997 | Bishop et al. |
| 5,662,667 A | 9/1997 | Knodel |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,678,748 A | 10/1997 | Plyley |
| 5,680,982 A | 10/1997 | Schulze et al. |
| 5,680,983 A | 10/1997 | Plyley et al. |
| 5,697,542 A | 12/1997 | Knodel et al. |
| 5,697,543 A | 12/1997 | Burdorff |
| 5,704,534 A | 1/1998 | Huitema et al. |
| 5,704,898 A | 1/1998 | Kokish |
| 5,706,998 A | 1/1998 | Blyley et al. |
| 5,709,334 A | 1/1998 | Sorrentino et al. |
| 5,713,505 A | 2/1998 | Huitema |
| 5,715,988 A | 2/1998 | Palmer |
| 5,718,359 A | 2/1998 | Palmer et al. |
| 5,732,871 A | 3/1998 | Clark et al. |
| 5,735,445 A | 4/1998 | Vidal et al. |
| 5,762,255 A | 6/1998 | Chrisman et al. |
| 5,762,256 A | 6/1998 | Mastri et al. |
| 5,779,130 A | 7/1998 | Alesi et al. |
| 5,782,396 A | 7/1998 | Mastri et al. |
| 5,782,397 A | 7/1998 | Koukline |
| 5,785,232 A | 7/1998 | Vidal et al. |
| 5,794,834 A | 8/1998 | Hamblin et al. |
| 5,797,536 A | 8/1998 | Smith et al. |
| 5,797,537 A | 8/1998 | Oberlin et al. |
| 5,797,538 A | 8/1998 | Heaton et al. |
| 5,810,240 A | 9/1998 | Robertson |
| 5,814,055 A | 9/1998 | Knodel et al. |
| 5,820,009 A | 10/1998 | Melling et al. |
| 5,829,662 A | 11/1998 | Allen et al. |
| 5,860,995 A | 1/1999 | Berkelaar |
| 5,865,361 A | 2/1999 | Milliman et al. |
| 5,878,937 A | 3/1999 | Green et al. |
| 5,878,938 A | 3/1999 | Bittner et al. |

(56) References Cited

U.S. PATENT DOCUMENTS

| | | |
|---|---|---|
| 5,893,506 A | 4/1999 | Powell |
| 5,894,979 A | 4/1999 | Powell |
| 5,901,895 A | 5/1999 | Heaton et al. |
| 5,918,791 A | 7/1999 | Sorrentino et al. |
| 5,931,847 A | 8/1999 | Bittner et al. |
| 5,954,259 A | 9/1999 | Viola et al. |
| 5,964,394 A | 10/1999 | Robertson |
| D416,089 S | 11/1999 | Barton et al. |
| 5,988,479 A | 11/1999 | Palmer |
| 6,032,849 A | 3/2000 | Mastri et al. |
| 6,053,390 A | 4/2000 | Green et al. |
| 6,079,606 A | 6/2000 | Milliman et al. |
| 6,109,500 A | 8/2000 | Alli et al. |
| 6,131,789 A | 10/2000 | Schulze et al. |
| 6,155,473 A | 12/2000 | Tompkins et al. |
| D441,865 S | 5/2001 | Racenet et al. |
| 6,241,139 B1 | 6/2001 | Milliman et al. |
| 6,250,532 B1 | 6/2001 | Green et al. |
| 6,264,087 B1 | 7/2001 | Whitman |
| 6,270,453 B1 | 8/2001 | Sakai |
| 6,325,810 B1 | 12/2001 | Hamilton et al. |
| 6,330,965 B1 | 12/2001 | Milliman et al. |
| 6,488,196 B1 | 12/2002 | Fenton, Jr. |
| 6,550,757 B2 | 4/2003 | Sesek |
| 6,569,171 B2 | 5/2003 | DeGuillebon et al. |
| 6,595,509 B2 | 7/2003 | Sesek |
| 6,619,529 B2 | 9/2003 | Green et al. |
| 6,644,532 B2 | 11/2003 | Green et al. |
| 6,669,073 B2 | 12/2003 | Milliman et al. |
| 6,716,233 B1 | 4/2004 | Whitman |
| 6,786,382 B1 | 9/2004 | Hoffman |
| 6,817,508 B1 | 11/2004 | Racenet et al. |
| 6,821,282 B2 | 11/2004 | Perry et al. |
| 6,835,199 B2 | 12/2004 | McGuckin, Jr. et al. |
| 6,913,181 B2 | 7/2005 | Mochizuki et al. |
| 6,923,360 B2 | 8/2005 | Sesek et al. |
| 6,953,138 B1 | 10/2005 | Dworak et al. |
| 6,953,139 B2 | 10/2005 | Milliman et al. |
| 6,964,363 B2 | 11/2005 | Wales et al. |
| 6,978,921 B2 | 12/2005 | Shelton, IV et al. |
| 6,986,451 B1 | 1/2006 | Mastri et al. |
| 6,988,649 B2 | 1/2006 | Shelton, IV et al. |
| 7,000,818 B2 | 2/2006 | Shelton, IV et al. |
| 7,044,352 B2 | 5/2006 | Shelton, IV et al. |
| 7,044,353 B2 | 5/2006 | Mastri et al. |
| 7,044,947 B2 | 5/2006 | de la Torre et al. |
| 7,055,730 B2 | 6/2006 | Ehrenfels et al. |
| 7,070,083 B2 | 7/2006 | Jankowski |
| 7,097,089 B2 | 8/2006 | Marczyk |
| 7,097,650 B2 | 8/2006 | Weller et al. |
| 7,108,472 B2 | 9/2006 | Norris et al. |
| 7,128,253 B2 | 10/2006 | Mastri et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,147,139 B2 | 12/2006 | Schwemberger et al. |
| 7,213,736 B2 | 5/2007 | Wales et al. |
| 7,225,964 B2 | 6/2007 | Mastri et al. |
| 7,237,708 B1 | 7/2007 | Guy et al. |
| 7,258,262 B2 | 8/2007 | Mastri et al. |
| 7,275,674 B2 | 10/2007 | Racenet et al. |
| 7,278,562 B2 | 10/2007 | Mastri et al. |
| 7,290,692 B2 | 11/2007 | Marks |
| 7,293,685 B2 | 11/2007 | Ehrenfels et al. |
| 7,303,107 B2 | 12/2007 | Milliman et al. |
| 7,308,998 B2 | 12/2007 | Mastri et al. |
| 7,328,828 B2 | 2/2008 | Ortiz et al. |
| 7,334,717 B2 | 2/2008 | Rethy et al. |
| 7,380,695 B2 | 6/2008 | Doll et al. |
| 7,380,696 B2 | 6/2008 | Shelton, IV et al. |
| 7,398,908 B2 | 7/2008 | Holsten et al. |
| 7,399,310 B2 | 7/2008 | Edoga et al. |
| 7,401,721 B2 | 7/2008 | Holsten et al. |
| 7,404,508 B2 | 7/2008 | Smith et al. |
| 7,407,075 B2 | 8/2008 | Holsten et al. |
| 7,407,078 B2 | 8/2008 | Shelton, IV et al. |
| 7,416,101 B2 | 8/2008 | Shelton, IV et al. |
| RE40,514 E | 9/2008 | Mastri et al. |
| 7,419,080 B2 | 9/2008 | Smith et al. |
| 7,419,081 B2 | 9/2008 | Ehrenfels et al. |
| 7,422,136 B1 | 9/2008 | Marczyk |
| 7,422,139 B2 | 9/2008 | Shelton, IV et al. |
| 7,431,188 B1 | 10/2008 | Marczyk |
| 7,434,715 B2 | 10/2008 | Shelton, IV et al. |
| 7,434,716 B2 | 10/2008 | Viola |
| 7,455,208 B2 | 11/2008 | Wales et al. |
| 7,455,676 B2 | 11/2008 | Holsten et al. |
| 7,461,767 B2 | 12/2008 | Viola et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,481,348 B2 | 1/2009 | Marczyk |
| 7,481,349 B2 | 1/2009 | Holsten et al. |
| 7,487,899 B2 | 2/2009 | Shelton, IV et al. |
| 7,490,749 B2 | 2/2009 | Schall et al. |
| 7,506,790 B2 | 3/2009 | Shelton, IV |
| 7,506,791 B2 | 3/2009 | Omaits et al. |
| 7,513,408 B2 | 4/2009 | Shelton, IV et al. |
| 7,530,484 B1 | 5/2009 | Durrani |
| 7,543,730 B1 | 6/2009 | Marczyk |
| 7,543,731 B2 | 6/2009 | Green et al. |
| 7,546,940 B2 | 6/2009 | Milliman et al. |
| 7,549,564 B2 | 6/2009 | Boudreaux |
| 7,552,854 B2 | 6/2009 | Wixey et al. |
| 7,556,186 B2 | 7/2009 | Milliman |
| 7,565,993 B2 | 7/2009 | Milliman et al. |
| 7,568,604 B2 | 8/2009 | Ehrenfels et al. |
| 7,588,174 B2 | 9/2009 | Holsten et al. |
| 7,588,175 B2 | 9/2009 | Timm et al. |
| 7,588,177 B2 | 9/2009 | Racenet |
| 7,604,151 B2 | 10/2009 | Hess et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,631,793 B2 | 12/2009 | Rethy et al. |
| 7,635,074 B2 | 12/2009 | Olson et al. |
| 7,637,409 B2 | 12/2009 | Marczyk |
| 7,637,410 B2 | 12/2009 | Marczyk |
| 7,641,091 B2 | 1/2010 | Olson et al. |
| 7,641,093 B2 | 1/2010 | Doll et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,665,647 B2 | 2/2010 | Shelton, IV et al. |
| 7,669,746 B2 | 3/2010 | Shelton, IV |
| 7,670,334 B2 * | 3/2010 | Hueil ............... A61B 17/07207 606/1 |
| 7,673,781 B2 | 3/2010 | Swayze et al. |
| 7,682,367 B2 | 3/2010 | Shah et al. |
| 7,690,547 B2 | 4/2010 | Racenet et al. |
| 7,703,653 B2 | 4/2010 | Shah et al. |
| 7,717,312 B2 | 5/2010 | Beetel |
| 7,721,931 B2 | 5/2010 | Shelton, IV et al. |
| 7,721,933 B2 | 5/2010 | Ehrenfels et al. |
| 7,721,935 B2 | 5/2010 | Racenet et al. |
| 7,721,936 B2 | 5/2010 | Shelton, IV et al. |
| 7,726,538 B2 | 6/2010 | Holsten et al. |
| 7,726,539 B2 | 6/2010 | Holsten et al. |
| 7,731,073 B2 | 6/2010 | Wixey et al. |
| 7,735,703 B2 | 6/2010 | Morgan et al. |
| 7,753,245 B2 | 7/2010 | Boudreaux et al. |
| 7,753,246 B2 | 7/2010 | Scirica |
| 7,757,925 B2 | 7/2010 | Viola et al. |
| 7,766,210 B2 | 8/2010 | Shelton, IV et al. |
| 7,770,774 B2 | 8/2010 | Mastri et al. |
| 7,780,054 B2 | 8/2010 | Wales |

(56) References Cited

U.S. PATENT DOCUMENTS

| | | |
|---|---|---|
| 7,780,055 B2 | 8/2010 | Scirica et al. |
| 7,784,662 B2 | 8/2010 | Wales et al. |
| 7,784,663 B2 | 8/2010 | Shelton, IV |
| 7,793,812 B2 | 9/2010 | Moore et al. |
| 7,798,386 B2 | 9/2010 | Schall et al. |
| 7,810,693 B2 | 10/2010 | Broehl et al. |
| 7,815,090 B2 | 10/2010 | Marczyk |
| 7,815,091 B2 | 10/2010 | Marczyk |
| 7,819,298 B2 | 10/2010 | Hall et al. |
| 7,819,896 B2 | 10/2010 | Racenet |
| 7,823,760 B2 | 11/2010 | Zemlok et al. |
| 7,828,188 B2 | 11/2010 | Jankowski |
| 7,828,189 B2 | 11/2010 | Holsten et al. |
| 7,837,079 B2 | 11/2010 | Holsten et al. |
| 7,837,081 B2 | 11/2010 | Holsten et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,857,184 B2 | 12/2010 | Viola |
| 7,857,185 B2 | 12/2010 | Swayze et al. |
| 7,857,187 B2 | 12/2010 | Milliman |
| 7,861,906 B2 | 1/2011 | Doll et al. |
| 7,866,525 B2 | 1/2011 | Scirica |
| 7,866,527 B2 | 1/2011 | Hall et al. |
| 7,891,534 B2 | 2/2011 | Wenchell et al. |
| 7,905,381 B2 | 3/2011 | Baxter, III et al. |
| 7,909,220 B2 | 3/2011 | Viola |
| 7,909,221 B2 | 3/2011 | Viola et al. |
| 7,913,891 B2 | 3/2011 | Doll et al. |
| 7,914,543 B2 | 3/2011 | Roth et al. |
| 7,918,230 B2 | 4/2011 | Whitman et al. |
| 7,918,376 B1 | 4/2011 | Knodel et al. |
| 7,918,377 B2 | 4/2011 | Measamer et al. |
| 7,922,063 B2 | 4/2011 | Zemlok et al. |
| 7,934,628 B2 | 5/2011 | Wenchell et al. |
| 7,934,629 B2 | 5/2011 | Wixey et al. |
| 7,934,630 B2 | 5/2011 | Shelton, IV et al. |
| 7,942,300 B2 | 5/2011 | Rethy et al. |
| 7,954,685 B2 | 6/2011 | Viola |
| 7,954,686 B2 | 6/2011 | Baxter, III et al. |
| 7,959,050 B2 | 6/2011 | Smith et al. |
| 7,963,433 B2 | 6/2011 | Whitman et al. |
| 7,992,758 B2 | 8/2011 | Whitman et al. |
| 8,002,795 B2 | 8/2011 | Beetel |
| 8,006,887 B2 | 8/2011 | Marczyk |
| 8,007,513 B2 | 8/2011 | Nalagatla et al. |
| 8,008,598 B2 | 8/2011 | Whitman et al. |
| 8,011,550 B2 | 9/2011 | Aranyi et al. |
| 8,011,553 B2 | 9/2011 | Mastri et al. |
| 8,012,170 B2 | 9/2011 | Whitman et al. |
| 8,016,178 B2 | 9/2011 | Olson et al. |
| 8,020,742 B2 | 9/2011 | Marczyk |
| 8,020,743 B2 | 9/2011 | Shelton, IV |
| 8,028,885 B2 | 10/2011 | Smith et al. |
| 8,033,438 B2 | 10/2011 | Scirica |
| 8,033,440 B2 | 10/2011 | Wenchell et al. |
| 8,033,441 B2 | 10/2011 | Marczyk |
| 8,033,442 B2 | 10/2011 | Racenet et al. |
| 8,034,077 B2 | 10/2011 | Smith et al. |
| 8,038,046 B2 | 10/2011 | Smith et al. |
| 8,052,024 B2 | 11/2011 | Viola et al. |
| 8,056,788 B2 | 11/2011 | Mastri et al. |
| 8,056,789 B1 | 11/2011 | White et al. |
| 8,061,576 B2 | 11/2011 | Cappola |
| 8,061,577 B2 | 11/2011 | Racenet et al. |
| 8,070,033 B2 | 12/2011 | Milliman et al. |
| 8,070,034 B1 | 12/2011 | Knodel |
| 8,070,035 B2 | 12/2011 | Holsten et al. |
| 8,070,036 B1 | 12/2011 | Knodel |
| 8,074,861 B2 | 12/2011 | Ehrenfels et al. |
| 8,083,118 B2 | 12/2011 | Milliman et al. |
| 8,087,563 B2 | 1/2012 | Milliman et al. |
| 8,091,753 B2 | 1/2012 | Viola |
| 8,091,754 B2 | 1/2012 | Ehrenfels et al. |
| 8,092,493 B2 | 1/2012 | Marczyk |
| 8,100,309 B2 | 1/2012 | Marczyk |
| 8,113,406 B2 | 2/2012 | Holsten et al. |
| 8,113,407 B2 | 2/2012 | Holsten et al. |
| 8,113,408 B2 | 2/2012 | Wenchell et al. |
| 8,113,410 B2 | 2/2012 | Hall et al. |
| 8,118,207 B2 | 2/2012 | Racenet et al. |
| 8,123,100 B2 | 2/2012 | Holsten et al. |
| 8,127,976 B2 | 3/2012 | Scirica et al. |
| 8,136,712 B2 | 3/2012 | Zingman |
| 8,152,041 B2 | 4/2012 | Kostrzewski |
| 8,157,145 B2 | 4/2012 | Shelton, IV et al. |
| 8,157,150 B2 | 4/2012 | Viola et al. |
| 8,157,152 B2 | 4/2012 | Holsten et al. |
| 8,181,839 B2 | 5/2012 | Beetel |
| 8,186,555 B2 | 5/2012 | Shelton, IV et al. |
| 8,186,556 B2 | 5/2012 | Viola |
| 8,186,560 B2 | 5/2012 | Hess et al. |
| 8,191,752 B2 | 6/2012 | Scirica |
| 8,196,795 B2 | 6/2012 | Moore et al. |
| 8,201,721 B2 | 6/2012 | Zemlok et al. |
| 8,205,619 B2 | 6/2012 | Shah et al. |
| 8,205,780 B2 | 6/2012 | Sorrentino et al. |
| 8,205,781 B2 | 6/2012 | Baxter, III et al. |
| 8,210,411 B2 | 7/2012 | Yates et al. |
| 8,210,416 B2 | 7/2012 | Milliman et al. |
| 8,220,688 B2 | 7/2012 | Laurent et al. |
| 8,225,979 B2 | 7/2012 | Farascioni et al. |
| 8,231,040 B2 | 7/2012 | Zemlok et al. |
| 8,231,041 B2 | 7/2012 | Marczyk et al. |
| 8,235,274 B2 | 8/2012 | Cappola |
| 8,236,010 B2 | 8/2012 | Ortiz et al. |
| 8,240,536 B2 | 8/2012 | Marczyk |
| 8,240,537 B2 | 8/2012 | Marczyk |
| 8,241,322 B2 | 8/2012 | Whitman et al. |
| 8,245,898 B2 | 8/2012 | Smith et al. |
| 8,245,899 B2 | 8/2012 | Swensgard et al. |
| 8,245,900 B2 | 8/2012 | Scirica |
| 8,256,656 B2 | 9/2012 | Milliman et al. |
| 8,272,552 B2 | 9/2012 | Holsten et al. |
| 8,272,554 B2 | 9/2012 | Whitman et al. |
| 8,281,972 B2 | 10/2012 | Wixey et al. |
| 8,281,973 B2 | 10/2012 | Wenchell et al. |
| 8,286,846 B2 | 10/2012 | Smith et al. |
| 8,292,146 B2 | 10/2012 | Holsten et al. |
| 8,292,148 B2 | 10/2012 | Viola |
| 8,292,151 B2 | 10/2012 | Viola |
| 8,292,152 B2 | 10/2012 | Milliman et al. |
| 8,292,153 B2 | 10/2012 | Jankowski |
| 8,292,157 B2 | 10/2012 | Smith et al. |
| 8,308,041 B2 | 11/2012 | Kostrzewski |
| 8,308,043 B2 | 11/2012 | Bindra et al. |
| 8,317,070 B2 | 11/2012 | Hueil et al. |
| 8,322,455 B2 | 12/2012 | Shelton, IV et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,342,380 B2 | 1/2013 | Viola |
| 8,348,125 B2 | 1/2013 | Viola et al. |
| 8,348,129 B2 | 1/2013 | Bedi et al. |
| 8,348,131 B2 | 1/2013 | Omaits et al. |
| 8,353,440 B2 | 1/2013 | Whitman et al. |
| 8,360,297 B2 | 1/2013 | Shelton, IV et al. |
| 8,360,299 B2 | 1/2013 | Zemlok et al. |
| 8,393,513 B2 | 3/2013 | Jankowski |
| 8,397,972 B2 | 3/2013 | Kostrzewski |
| 8,397,973 B1 | 3/2013 | Hausen |
| 8,403,198 B2 | 3/2013 | Sorrentino et al. |
| 8,413,868 B2 | 4/2013 | Cappola |
| 8,414,577 B2 | 4/2013 | Boudreaux et al. |
| 8,418,906 B2 | 4/2013 | Farascioni et al. |
| 8,418,907 B2 | 4/2013 | Johnson et al. |
| 8,418,908 B1 | 4/2013 | Beardsley |
| 8,419,768 B2 | 4/2013 | Marczyk |
| 8,439,246 B1 | 5/2013 | Knodel |
| 8,444,036 B2 | 5/2013 | Shelton, IV |
| 8,453,907 B2 | 6/2013 | Laurent et al. |
| 8,453,912 B2 | 6/2013 | Mastri et al. |
| 8,453,913 B2 | 6/2013 | Milliman |

(56) References Cited

U.S. PATENT DOCUMENTS

| | | |
|---|---|---|
| 8,459,520 B2 | 6/2013 | Giordano et al. |
| 8,459,522 B2 | 6/2013 | Marczyk |
| 8,464,922 B2 | 6/2013 | Marczyk |
| 8,469,252 B2 | 6/2013 | Holcomb et al. |
| 8,479,967 B2 | 7/2013 | Marczyk |
| 8,496,152 B2 | 7/2013 | Viola |
| 8,496,155 B2 | 7/2013 | Knodel |
| 8,496,156 B2 | 7/2013 | Sniffin et al. |
| 8,496,683 B2 | 7/2013 | Prommersberger et al. |
| 8,505,799 B2 | 8/2013 | Viola et al. |
| 8,505,801 B2 | 8/2013 | Ehrenfels et al. |
| 8,517,239 B2 | 8/2013 | Scheib et al. |
| 8,517,240 B1 | 8/2013 | Mata et al. |
| 8,523,043 B2 | 9/2013 | Ullrich et al. |
| 8,540,130 B2 | 9/2013 | Moore et al. |
| 8,540,133 B2 | 9/2013 | Bedi et al. |
| 8,540,625 B2 | 9/2013 | Miyoshi |
| 8,544,712 B2 | 10/2013 | Jankowski |
| 8,556,151 B2 | 10/2013 | Viola |
| 8,556,152 B2 | 10/2013 | Marczyk et al. |
| 8,556,153 B1 | 10/2013 | Knodel |
| 8,561,871 B2 | 10/2013 | Rajappa et al. |
| 8,561,874 B2 | 10/2013 | Scirica |
| 8,573,459 B2 | 11/2013 | Smith et al. |
| 8,573,460 B2 | 11/2013 | Cappola |
| 8,573,462 B2 | 11/2013 | Smith et al. |
| 8,573,463 B2 | 11/2013 | Scirica et al. |
| 8,573,464 B2 | 11/2013 | Nalagatla et al. |
| 8,579,176 B2 | 11/2013 | Smith et al. |
| 8,579,177 B2 | 11/2013 | Beetel |
| 8,584,919 B2 | 11/2013 | Hueil et al. |
| 8,584,921 B2 | 11/2013 | Scirica |
| 8,596,513 B2 | 12/2013 | Olson |
| 8,608,043 B2 | 12/2013 | Scirica |
| 8,608,045 B2 | 12/2013 | Smith et al. |
| 8,616,427 B2 | 12/2013 | Viola |
| 8,622,274 B2 | 1/2014 | Yates et al. |
| 8,627,992 B2 | 1/2014 | Edoga et al. |
| 8,627,993 B2 | 1/2014 | Smith et al. |
| 8,627,995 B2 | 1/2014 | Smith et al. |
| 8,631,990 B1 | 1/2014 | Park et al. |
| 8,632,525 B2 | 1/2014 | Kerr et al. |
| 8,632,535 B2 | 1/2014 | Shelton, IV et al. |
| 8,636,189 B1 | 1/2014 | Knodel et al. |
| 8,636,190 B2 | 1/2014 | Zemlok et al. |
| 8,636,192 B2 | 1/2014 | Farascioni et al. |
| 8,636,193 B2 | 1/2014 | Whitman et al. |
| 8,636,762 B2 | 1/2014 | Whitman et al. |
| 8,636,766 B2 | 1/2014 | Milliman et al. |
| 8,657,174 B2 | 2/2014 | Yates et al. |
| 8,657,176 B2 | 2/2014 | Shelton, IV et al. |
| 8,657,178 B2 | 2/2014 | Hueil et al. |
| 8,672,209 B2 | 3/2014 | Crainich |
| 8,672,951 B2 | 3/2014 | Smith et al. |
| 8,685,004 B2 | 4/2014 | Zemlock et al. |
| 8,695,865 B2 | 4/2014 | Smith et al. |
| 8,696,665 B2 | 4/2014 | Hunt et al. |
| 8,708,211 B2 | 4/2014 | Zemlok et al. |
| 8,708,213 B2 | 4/2014 | Shelton, IV et al. |
| 8,740,034 B2 | 6/2014 | Morgan et al. |
| 8,740,035 B2 | 6/2014 | Mastri et al. |
| 8,740,036 B2 | 6/2014 | Williams |
| 8,752,748 B2 | 6/2014 | Whitman et al. |
| 8,763,876 B2 | 7/2014 | Kostrzewski |
| 8,770,458 B2 | 7/2014 | Scirica |
| 8,770,459 B2 | 7/2014 | Racenet et al. |
| 8,789,741 B2 | 7/2014 | Baxter, III et al. |
| 8,800,839 B2 | 8/2014 | Beetel |
| 8,800,840 B2 | 8/2014 | Jankowski |
| 8,800,841 B2 | 8/2014 | Ellerhorst et al. |
| 8,806,973 B2 | 8/2014 | Ross et al. |
| 8,807,414 B2 | 8/2014 | Ross et al. |
| 8,820,603 B2 | 9/2014 | Shelton, IV et al. |
| 8,820,608 B2 | 9/2014 | Miyamoto |
| 8,833,631 B2 | 9/2014 | Munro, III et al. |
| 8,840,003 B2 | 9/2014 | Morgan et al. |
| 8,858,571 B2 | 10/2014 | Shelton, IV et al. |
| 8,864,010 B2 * | 10/2014 | Williams ......... A61B 17/07207 |
| | | 227/175.1 |
| 8,875,971 B2 | 11/2014 | Hall et al. |
| 8,875,972 B2 | 11/2014 | Weisenburgh, II et al. |
| 8,887,979 B2 | 11/2014 | Mastri et al. |
| 8,899,462 B2 | 12/2014 | Kostrzewski et al. |
| 8,899,463 B2 | 12/2014 | Schall et al. |
| 8,905,288 B2 | 12/2014 | Wenchell |
| 8,920,435 B2 | 12/2014 | Smith et al. |
| 8,925,783 B2 | 1/2015 | Zemlok et al. |
| 8,931,679 B2 | 1/2015 | Kostrzewski |
| 8,931,683 B2 | 1/2015 | Racenet et al. |
| 8,939,343 B2 | 1/2015 | Milliman et al. |
| 8,967,444 B2 | 3/2015 | Beetel |
| 8,967,446 B2 | 3/2015 | Beardsley et al. |
| 8,967,447 B2 | 3/2015 | Hartoumbekis |
| 8,968,276 B2 | 3/2015 | Zemlok et al. |
| 8,973,803 B2 | 3/2015 | Hall et al. |
| 8,979,827 B2 | 3/2015 | Cappola |
| 9,004,340 B2 | 4/2015 | Scirica |
| 9,010,611 B2 | 4/2015 | Ross et al. |
| 9,016,541 B2 | 4/2015 | Viola et al. |
| 9,016,545 B2 | 4/2015 | Aranyi et al. |
| 9,022,271 B2 | 5/2015 | Scirica |
| 9,023,014 B2 | 5/2015 | Chowaniec et al. |
| 9,027,817 B2 | 5/2015 | Milliman et al. |
| 9,027,818 B2 | 5/2015 | Scirica et al. |
| 9,033,202 B2 | 5/2015 | Scirica |
| 9,038,880 B1 | 5/2015 | Donohoe |
| 9,055,943 B2 | 6/2015 | Zemlok et al. |
| 9,072,515 B2 | 7/2015 | Hall et al. |
| 9,084,601 B2 | 7/2015 | Moore et al. |
| 9,101,358 B2 | 8/2015 | Kerr et al. |
| 9,149,324 B2 * | 10/2015 | Huang ............ A61B 18/1445 |
| 9,161,813 B2 | 10/2015 | Benamou |
| 9,204,876 B2 | 12/2015 | Cappola et al. |
| 9,237,890 B2 | 1/2016 | Kostrzewski |
| 9,265,585 B2 | 2/2016 | Wingardner et al. |
| 9,282,966 B2 | 3/2016 | Shelton, IV et al. |
| 9,295,514 B2 * | 3/2016 | Shelton, IV ......... A61B 18/082 |
| 9,386,984 B2 | 7/2016 | Aronhalt et al. |
| 9,402,629 B2 | 8/2016 | Ehrenfels et al. |
| 9,510,830 B2 | 12/2016 | Shelton, IV et al. |
| 9,532,782 B2 | 1/2017 | Kostrzewski |
| 9,662,108 B2 | 5/2017 | Williams |
| 9,693,774 B2 * | 7/2017 | Gettinger ......... A61B 17/07292 |
| 9,737,302 B2 | 8/2017 | Shelton, IV et al. |
| 9,737,303 B2 | 8/2017 | Shelton, IV et al. |
| 9,797,486 B2 | 10/2017 | Zergiebel et al. |
| 10,363,037 B2 * | 7/2019 | Aronhalt .......... A61B 17/07207 |
| 10,492,785 B2 * | 12/2019 | Overmyer .............. A61B 34/30 |
| 10,743,873 B2 * | 8/2020 | Overmyer ......... A61B 17/07207 |
| 2002/0025243 A1 | 2/2002 | Heck |
| 2002/0029044 A1 | 3/2002 | Monassevitch et al. |
| 2002/0062136 A1 | 5/2002 | Hillstead |
| 2002/0120279 A1 | 8/2002 | Deguillebon et al. |
| 2003/0130677 A1 | 7/2003 | Whitman et al. |
| 2004/0006372 A1 | 1/2004 | Racenet et al. |
| 2005/0234478 A1 | 10/2005 | Wixey |
| 2006/0097026 A1 | 5/2006 | Shelton, IV |
| 2006/0100644 A1 | 5/2006 | Viola |
| 2006/0180634 A1 | 8/2006 | Shelton et al. |
| 2006/0235442 A1 | 10/2006 | Huitema |
| 2006/0289602 A1 | 12/2006 | Wales et al. |
| 2007/0027469 A1 * | 2/2007 | Smith ............ A61B 17/07207 |
| | | 606/205 |
| 2007/0034664 A1 | 2/2007 | Jiang |
| 2007/0039997 A1 | 2/2007 | Mather et al. |
| 2007/0057014 A1 | 3/2007 | Whitman et al. |
| 2007/0068990 A1 | 3/2007 | Shelton, IV et al. |
| 2007/0084897 A1 | 4/2007 | Shelton, IV et al. |
| 2007/0102472 A1 | 5/2007 | Shelton, IV |
| 2007/0119901 A1 | 5/2007 | Ehrenfels et al. |
| 2007/0131732 A1 | 6/2007 | Holsten et al. |
| 2007/0175950 A1 | 8/2007 | Shelton, IV et al. |
| 2007/0175951 A1 | 8/2007 | Shelton, IV et al. |
| 2008/0029574 A1 | 2/2008 | Shelton et al. |

(56) References Cited

U.S. PATENT DOCUMENTS

| | | |
|---|---|---|
| 2008/0029575 A1 | 2/2008 | Shelton et al. |
| 2008/0041918 A1 | 2/2008 | Holsten et al. |
| 2008/0078807 A1 | 4/2008 | Hess et al. |
| 2008/0083807 A1 | 4/2008 | Beardsley et al. |
| 2008/0083809 A1* | 4/2008 | Scirica ............... A61B 17/068 227/175.1 |
| 2008/0169333 A1 | 7/2008 | Shelton et al. |
| 2008/0179375 A1 | 7/2008 | Scirica |
| 2008/0255607 A1 | 10/2008 | Zemlok |
| 2009/0001129 A1 | 1/2009 | Marczyk |
| 2009/0001130 A1 | 1/2009 | Hess et al. |
| 2009/0026245 A1 | 1/2009 | Holsten et al. |
| 2009/0048589 A1 | 2/2009 | Takashino et al. |
| 2009/0057369 A1 | 3/2009 | Smith et al. |
| 2009/0090763 A1 | 4/2009 | Zemlok et al. |
| 2009/0198272 A1 | 8/2009 | Kerver et al. |
| 2009/0206131 A1 | 8/2009 | Weisenburgh, II et al. |
| 2009/0206133 A1 | 8/2009 | Morgan et al. |
| 2009/0206137 A1 | 8/2009 | Hall et al. |
| 2009/0277948 A1 | 11/2009 | Beardsley et al. |
| 2009/0277949 A1 | 11/2009 | Viola et al. |
| 2010/0069942 A1 | 3/2010 | Shelton, IV |
| 2010/0072258 A1 | 3/2010 | Farascioni et al. |
| 2010/0089970 A1 | 4/2010 | Smith et al. |
| 2010/0193566 A1 | 8/2010 | Scheib et al. |
| 2010/0230465 A1 | 9/2010 | Smith et al. |
| 2010/0331820 A1 | 12/2010 | Prisco et al. |
| 2011/0036892 A1 | 2/2011 | Marczyk et al. |
| 2011/0042440 A1 | 2/2011 | Holsten et al. |
| 2011/0087276 A1 | 4/2011 | Bedi et al. |
| 2011/0108601 A1 | 5/2011 | Clark et al. |
| 2011/0108603 A1 | 5/2011 | Racenet et al. |
| 2011/0121049 A1 | 5/2011 | Malinouskas et al. |
| 2011/0125138 A1 | 5/2011 | Malinouskas et al. |
| 2011/0127185 A1 | 6/2011 | Ward |
| 2011/0139852 A1 | 6/2011 | Zingman |
| 2011/0147433 A1 | 6/2011 | Shelton, IV et al. |
| 2011/0155787 A1 | 6/2011 | Laurent et al. |
| 2011/0290853 A1 | 12/2011 | Shelton, IV et al. |
| 2012/0061446 A1 | 3/2012 | Knodel et al. |
| 2012/0074198 A1 | 3/2012 | Huitema et al. |
| 2012/0074200 A1 | 3/2012 | Schmid et al. |
| 2012/0078243 A1 | 3/2012 | Worrell et al. |
| 2012/0080482 A1 | 4/2012 | Schall et al. |
| 2012/0080498 A1 | 4/2012 | Shelton, IV et al. |
| 2012/0091182 A1 | 4/2012 | Marczyk |
| 2012/0168487 A1 | 7/2012 | Holsten et al. |
| 2012/0193396 A1 | 8/2012 | Zemlok et al. |
| 2012/0203247 A1 | 8/2012 | Shelton, IV et al. |
| 2012/0211542 A1 | 8/2012 | Racenet |
| 2012/0239009 A1 | 9/2012 | Mollere et al. |
| 2012/0286022 A1 | 11/2012 | Olson et al. |
| 2012/0318844 A1 | 12/2012 | Shelton, IV et al. |
| 2012/0325893 A1 | 12/2012 | Pastorelli et al. |
| 2013/0001270 A1 | 1/2013 | Kostrzewski |
| 2013/0012958 A1 | 1/2013 | Marczyk et al. |
| 2013/0015229 A1 | 1/2013 | Viola |
| 2013/0015230 A1 | 1/2013 | Wixey et al. |
| 2013/0015232 A1 | 1/2013 | Smith et al. |
| 2013/0015233 A1 | 1/2013 | Viola |
| 2013/0020375 A1 | 1/2013 | Shelton, IV et al. |
| 2013/0037595 A1 | 2/2013 | Gupta et al. |
| 2013/0048697 A1 | 2/2013 | Shelton, IV et al. |
| 2013/0056521 A1 | 3/2013 | Swensgard |
| 2013/0079814 A1 | 3/2013 | Hess et al. |
| 2013/0087603 A1 | 4/2013 | Viola |
| 2013/0092717 A1 | 4/2013 | Marczyk et al. |
| 2013/0098964 A1 | 4/2013 | Smith et al. |
| 2013/0098965 A1 | 4/2013 | Kostrzewski et al. |
| 2013/0098969 A1 | 4/2013 | Scirica et al. |
| 2013/0105545 A1 | 5/2013 | Burbank |
| 2013/0105547 A1 | 5/2013 | Beardsley |
| 2013/0105548 A1 | 5/2013 | Hodgkinson et al. |
| 2013/0105549 A1 | 5/2013 | Holsten et al. |
| 2013/0112730 A1 | 5/2013 | Whitman et al. |
| 2013/0112731 A1 | 5/2013 | Hodgkinson |
| 2013/0126583 A1 | 5/2013 | Hueil et al. |
| 2013/0126586 A1 | 5/2013 | Zhang et al. |
| 2013/0146640 A1 | 6/2013 | Jankowski |
| 2013/0172928 A1 | 7/2013 | Kostrzewski |
| 2013/0172929 A1 | 7/2013 | Hess et al. |
| 2013/0175317 A1 | 7/2013 | Yates et al. |
| 2013/0175322 A1 | 7/2013 | Yates et al. |
| 2013/0184718 A1 | 7/2013 | Smith et al. |
| 2013/0186931 A1 | 7/2013 | Beardsley |
| 2013/0186932 A1 | 7/2013 | Shelton, IV et al. |
| 2013/0186933 A1 | 7/2013 | Shelton, IV et al. |
| 2013/0193188 A1 | 8/2013 | Shelton, IV et al. |
| 2013/0200132 A1 | 8/2013 | Moore et al. |
| 2013/0206816 A1 | 8/2013 | Penna |
| 2013/0214025 A1 | 8/2013 | Zemlok et al. |
| 2013/0221065 A1 | 8/2013 | Aronhalt et al. |
| 2013/0240604 A1 | 9/2013 | Knodel |
| 2013/0248582 A1 | 9/2013 | Scirica |
| 2013/0256370 A1 | 10/2013 | Smith et al. |
| 2013/0256371 A1 | 10/2013 | Shelton, IV |
| 2013/0270321 A1 | 10/2013 | Marczyk |
| 2013/0270323 A1 | 10/2013 | Marczyk |
| 2013/0284789 A1 | 10/2013 | Smith et al. |
| 2013/0284791 A1 | 10/2013 | Olson et al. |
| 2013/0299552 A1 | 11/2013 | Viola |
| 2013/0306702 A1 | 11/2013 | Viola et al. |
| 2013/0306703 A1 | 11/2013 | Ehrenfels et al. |
| 2013/0306706 A1 | 11/2013 | Knodel |
| 2013/0313303 A1 | 11/2013 | Shelton, IV et al. |
| 2013/0032781 A1 | 12/2013 | Swayze et al. |
| 2013/0327809 A1 | 12/2013 | Shelton, IV et al. |
| 2013/0334278 A1 | 12/2013 | Kerr et al. |
| 2013/0334280 A1 | 12/2013 | Krehel et al. |
| 2013/0334281 A1 | 12/2013 | Williams |
| 2013/0334283 A1 | 12/2013 | Swayze et al. |
| 2013/0334284 A1 | 12/2013 | Swayze et al. |
| 2013/0334285 A1 | 12/2013 | Swayze et al. |
| 2013/0334286 A1 | 12/2013 | Swayze et al. |
| 2013/0334287 A1 | 12/2013 | Shelton, IV |
| 2013/0334288 A1 | 12/2013 | Shelton, IV |
| 2014/0014704 A1 | 1/2014 | Onukuri et al. |
| 2014/0014707 A1 | 1/2014 | Onukuri et al. |
| 2014/0021239 A1 | 1/2014 | Kostrzewski |
| 2014/0025046 A1 | 1/2014 | Williams et al. |
| 2014/0027491 A1 | 1/2014 | Beardsley et al. |
| 2014/0027493 A1 | 1/2014 | Jankowski |
| 2014/0042204 A1 | 2/2014 | Beetel |
| 2014/0103092 A1 | 4/2014 | Kostrzewski et al. |
| 2014/0103093 A1 | 4/2014 | Koch, Jr. et al. |
| 2014/0107640 A1 | 4/2014 | Yates et al. |
| 2014/0110453 A1 | 4/2014 | Wingardner et al. |
| 2014/0131416 A1 | 5/2014 | Whitman et al. |
| 2014/0135832 A1 | 5/2014 | Park et al. |
| 2014/0151433 A1 | 6/2014 | Shelton, IV et al. |
| 2014/0151434 A1 | 6/2014 | Shelton, IV et al. |
| 2014/0158746 A1 | 6/2014 | Mastri et al. |
| 2014/0166727 A1 | 6/2014 | Swayze et al. |
| 2014/0175146 A1 | 6/2014 | Knodel |
| 2014/0175149 A1 | 6/2014 | Smith et al. |
| 2014/0203063 A1 | 7/2014 | Hessler et al. |
| 2014/0205637 A1 | 7/2014 | Widenhouse et al. |
| 2014/0224856 A1 | 8/2014 | Smith et al. |
| 2014/0236173 A1 | 8/2014 | Scirica et al. |
| 2014/0236184 A1 | 8/2014 | Leimbach |
| 2014/0239038 A1 | 8/2014 | Leimbach et al. |
| 2014/0239041 A1 | 8/2014 | Zerkle et al. |
| 2014/0239044 A1 | 8/2014 | Hoffman |
| 2014/0246474 A1 | 9/2014 | Hall et al. |
| 2014/0246475 A1 | 9/2014 | Hall et al. |
| 2014/0246478 A1 | 9/2014 | Baber et al. |
| 2014/0246479 A1 | 9/2014 | Baber et al. |
| 2014/0260746 A1 | 9/2014 | Sakaguchi et al. |
| 2014/0263537 A1 | 9/2014 | Leimbach et al. |
| 2014/0263539 A1 | 9/2014 | Leimbach et al. |
| 2014/0263541 A1 | 9/2014 | Leimbach et al. |
| 2014/0263542 A1 | 9/2014 | Leimbach et al. |
| 2014/0263543 A1 | 9/2014 | Leimbach et al. |
| 2014/0263545 A1 | 9/2014 | Williams et al. |

(56) References Cited

U.S. PATENT DOCUMENTS

| | | |
|---|---|---|
| 2014/0263546 A1 | 9/2014 | Aranyi |
| 2014/0263550 A1 | 9/2014 | Aranyi et al. |
| 2014/0263553 A1 | 9/2014 | Leimbach et al. |
| 2014/0263554 A1 | 9/2014 | Leimbach et al. |
| 2014/0263555 A1 | 9/2014 | Hufnagel et al. |
| 2014/0263559 A1 | 9/2014 | Williams et al. |
| 2014/0263562 A1 | 9/2014 | Patel et al. |
| 2014/0263564 A1 | 9/2014 | Leimbach et al. |
| 2014/0263565 A1 | 9/2014 | Lytle, IV et al. |
| 2014/0263566 A1 | 9/2014 | Williams et al. |
| 2014/0263567 A1 | 9/2014 | Williams et al. |
| 2014/0263568 A1 | 9/2014 | Williams et al. |
| 2014/0263569 A1 | 9/2014 | Williams et al. |
| 2014/0263570 A1 | 9/2014 | Hopkins et al. |
| 2014/0263571 A1 | 9/2014 | Morgan et al. |
| 2014/0263572 A1 | 9/2014 | Shelton, IV et al. |
| 2014/0284372 A1 | 9/2014 | Kostrzewski |
| 2014/0291378 A1 | 10/2014 | Shelton, IV et al. |
| 2014/0299649 A1 | 10/2014 | Shelton, IV et al. |
| 2014/0305986 A1 | 10/2014 | Hall et al. |
| 2014/0305988 A1 | 10/2014 | Boudreaux et al. |
| 2014/0305992 A1 | 10/2014 | Kimsey et al. |
| 2014/0305994 A1 | 10/2014 | Parihar et al. |
| 2014/0353359 A1 | 12/2014 | Hall et al. |
| 2015/0008248 A1 | 1/2015 | Giordano et al. |
| 2015/0034697 A1 | 2/2015 | Mastri et al. |
| 2015/0041518 A1 | 2/2015 | Shelton, IV et al. |
| 2015/0053738 A1 | 2/2015 | Morgan et al. |
| 2015/0053740 A1 | 2/2015 | Shelton, IV |
| 2015/0053741 A1 | 2/2015 | Shelton, IV et al. |
| 2015/0053742 A1 | 2/2015 | Shelton, IV et al. |
| 2015/0053743 A1 | 2/2015 | Yates et al. |
| 2015/0053744 A1 | 2/2015 | Swayze et al. |
| 2015/0053745 A1 | 2/2015 | Yates et al. |
| 2015/0053746 A1 | 2/2015 | Shelton, IV et al. |
| 2015/0053748 A1 | 2/2015 | Yates et al. |
| 2015/0053749 A1 | 2/2015 | Shelton, IV et al. |
| 2015/0054753 A1 | 2/2015 | Morgan et al. |
| 2015/0007621 A1 | 3/2015 | Shelton, IV et al. |
| 2015/0060516 A1 | 3/2015 | Collings et al. |
| 2015/0060517 A1 | 3/2015 | Williams |
| 2015/0060521 A1 | 3/2015 | Weisenburgh, II et al. |
| 2015/0076205 A1 | 3/2015 | Zergiebel |
| 2015/0076206 A1 | 3/2015 | Sapre |
| 2015/0076209 A1 | 3/2015 | Shelton, IV et al. |
| 2015/0076212 A1 | 3/2015 | Shelton, IV |
| 2015/0083781 A1 | 3/2015 | Giordano et al. |
| 2015/0083783 A1 | 3/2015 | Shelton, IV et al. |
| 2015/0090760 A1 | 4/2015 | Giordano et al. |
| 2015/0090761 A1 | 4/2015 | Giordano et al. |
| 2015/0090762 A1 | 4/2015 | Giordano et al. |
| 2015/0090764 A1 | 4/2015 | Zemlok et al. |
| 2015/0108201 A1 | 4/2015 | Williams |
| 2015/0122872 A1 | 5/2015 | Olson et al. |
| 2015/0127046 A1 | 5/2015 | Peterson |
| 2015/0129631 A1 | 5/2015 | Beetel |
| 2015/0129634 A1 | 5/2015 | Shelton, IV et al. |
| 2015/0133995 A1 | 5/2015 | Shelton, IV et al. |
| 2015/0133996 A1 | 5/2015 | Shelton, IV et al. |
| 2015/0134076 A1 | 5/2015 | Shelton, IV et al. |
| 2015/0144678 A1 | 5/2015 | Hall et al. |
| 2015/0201935 A1 | 7/2015 | Weisenburgh, II et al. |
| 2015/0208902 A1 | 7/2015 | Okamoto |
| 2015/0245834 A1 | 9/2015 | Scirica et al. |
| 2015/0272576 A1 | 10/2015 | Cappola |
| 2015/0289873 A1 | 10/2015 | Shelton, IV et al. |
| 2015/0297221 A1 | 10/2015 | Kerr et al. |
| 2015/0297233 A1 | 10/2015 | Huitema et al. |
| 2016/0000439 A1 | 1/2016 | Weisenburgh, II et al. |
| 2016/0000440 A1 | 1/2016 | Weisenburgh, II et al. |
| 2016/0058447 A1 | 3/2016 | Posada et al. |
| 2016/0058492 A1 | 3/2016 | Yates et al. |
| 2016/0183948 A1 | 6/2016 | Shelton, IV et al. |
| 2016/0310204 A1 | 10/2016 | McHenry et al. |
| 2016/0338702 A1 | 11/2016 | Ehrenfels et al. |
| 2016/0374672 A1 | 12/2016 | Bear et al. |
| 2016/0374675 A1 | 12/2016 | Shelton, IV et al. |
| 2017/0007241 A1 | 1/2017 | Shelton, IV et al. |
| 2017/0007242 A1 | 1/2017 | Shelton, IV et al. |
| 2017/0007243 A1 | 1/2017 | Shelton, IV et al. |
| 2017/0007249 A1 | 1/2017 | Shelton, IV et al. |
| 2017/0231633 A1 | 8/2017 | Marczyk et al. |
| 2017/0245856 A1 | 8/2017 | Baxter, III et al. |
| 2017/0245858 A1 | 8/2017 | Williams |
| 2017/0281161 A1 | 10/2017 | Shelton, IV et al. |
| 2017/0281165 A1 | 10/2017 | Harris et al. |
| 2017/0281168 A1 | 10/2017 | Shelton, IV et al. |
| 2017/0290583 A1 | 10/2017 | Reed et al. |
| 2017/0290584 A1 | 10/2017 | Jasemian et al. |

FOREIGN PATENT DOCUMENTS

| | | |
|---|---|---|
| EP | 0 514 139 A2 | 11/1992 |
| EP | 0 536 903 A2 | 4/1993 |
| EP | 0 596 543 A1 | 5/1994 |
| EP | 1 523 944 A1 | 4/2005 |
| EP | 1 759 812 A1 | 3/2007 |
| EP | 1 915 953 A1 | 4/2008 |
| EP | 1 479 348 B1 | 7/2008 |
| EP | 2 005 902 A2 | 12/2008 |
| EP | 2 090 241 A1 | 8/2009 |
| EP | 2 263 568 A2 | 12/2010 |
| EP | 2 361 562 A1 | 8/2011 |
| EP | 2 462 875 A2 | 6/2012 |
| EP | 2 486 859 A2 | 8/2012 |
| EP | 2 764 833 A2 | 8/2014 |
| EP | 2 772 192 A1 | 9/2014 |
| EP | 2 777 530 A1 | 9/2014 |
| EP | 2 923 661 A2 | 3/2015 |
| EP | 2 891 462 A1 | 7/2015 |
| EP | 2 926 742 A1 | 10/2015 |
| EP | 2 942 020 A2 | 11/2015 |
| EP | 3 135 225 A2 | 3/2017 |
| EP | 3 238 639 A2 | 3/2017 |
| EP | 3 338 653 A1 | 6/2018 |
| EP | 3 338 698 A1 | 6/2018 |
| EP | 3 338 702 A1 | 6/2018 |
| JP | 2001-087272 A | 4/2001 |
| RU | 2063710 | 7/1996 |
| WO | WO 83/02247 A1 | 7/1983 |
| WO | WO 94/24947 A1 | 11/1994 |
| WO | WO 02/30296 A2 | 4/2002 |
| WO | WO 02/096327 A2 | 12/2002 |
| WO | WO 2003/094747 A1 | 11/2003 |
| WO | WO 2004/032762 A1 | 4/2004 |
| WO | WO 2012/052729 A1 | 4/2012 |
| WO | WO 2014/139440 A1 | 9/2014 |

OTHER PUBLICATIONS

European Patent Office, Extended European Search Report for European Application No. EP 20197859.0, entitled "Surgical Stapler with Circumferential Firing," dated Jan. 28, 2021, 13 pgs.
European Patent Office, The International Search Report and Written Opinion of the International Searching Authority for International Application No. PCT/US2016/045993 titled "Surgical Stapler Having Locking Articulation Joint", dated Jan. 24, 2017, 20 pgs.
Ethicon Endo Surgery, Inc., Contour Curved Cutter Stapler, 2014, 2 pgs.
Justright Surgical, JustRight Surgery, Dec. 31, 2014, 2 pgs.
European Patent Office, The International Search Report and the Written Opinion of the International Searching Authority for International Application No. PCT/US2014/028811, entitled "Surgical Stapler Having Actuation Mechanism with Rotatable Shaft," dated Aug. 5, 2014, 14 pgs.
The International Bureau of WIPO, International Preliminary Report on Patentability, for International Application No. PCT/US2014/028811, entitled "Surgical Stapler Having Actuation Mechanism with Rotatable Shaft," dated Sep. 15, 2015, 11 pgs.
European Patent Office, European Search Report for European Application No. EP 14764812.5, entitled "Surgical Stapler Having

(56) References Cited

OTHER PUBLICATIONS

Actuation Mechanism with Rotatable Shaft," dated Apr. 6, 2017, 6 pgs.
International Searching Authority/ EPO, Invitation to Pay Additional Fees and Communication Relating to the Results of the Partial International Search for PCT/US2017/027269, entitled "Reload Shaft Assembly for Surgical Stapler," dated Jun. 28, 2017, 15 pgs.
International Searching Authority/ EPO, Invitation to Pay Additional Fees and Communication Relating to the Results of the Partial International Search for PCT/US2017/027213, entitled "Surgical Stapler Having a Powered Handle," dated Jul. 5, 2017, 11 pgs.
International Searching Authority/ EPO, Invitation to Pay Additional Fees and Communication Relating to the Results of the Partial International Search for PCT/US2017/027142, entitled "Surgical Stapler Having Articulation Mechanism," dated Jul. 10, 2017, 15 pgs.
European Patent Office, The International Search Report and the Written Opinion of the International Searching Authority for International Application No. PCT/US2017/027269, entitled "Reload Shaft Assembly for Surgical Stapler," dated Sep. 12, 2017, 22 pgs.
European Patent Office, The International Search Report and the Written Opinion of the International Searching Authority for International Application No. PCT/US2017/027213, entitled "Surgical Stapler Having a Powered Handle," dated Sep. 13, 2017, 17 pgs.
European Patent Office, The International Search Report and the Written Opinion of the International Searching Authority for International Application No. PCT/US2017/027142, entitled "Surgical Stapler Having Articulation Mechanism," dated Sep. 14, 2017, 21 pgs.
The International Bureau of WIPO, International Preliminary Report on Patentability, for International Application No. PCT/US2016/045993, entitled "Surgical Stapler Having Locking Articulation Joint," dated Feb. 15, 2018, 13 pgs.
European Patent Office, European Search Report for European Application No. 07784007.2, entitled "Surgical Stapler," dated Jun. 15, 2012, 6 pgs.
International Searching Authority, U.S., The International Search Report and the Written Opinion of the International Searching authority for international application PCT/US2014/027768, titled "Surgical Stapler with Expandable Jaw", dated Jul. 25, 2014, 17 pgs.
European Patent Office, International Search Report and Written Opinion for International Application No. PCT/US2014/028211, entitled "Surgical Stapler with Partial Pockets," dated Sep. 8, 2014, 17 pgs.
International Searching Authority, U.S., The International Search Report and the Written Opinion of the International Searching authority for international application PCT/US2015/0035379, titled "Surgical Stapler with Circumferential Firing", dated Sep. 15, 2015,22 pgs.
The International Bureau of WIPO, International Preliminary Report on Patentability, for International Application No. PCT/US2014/027768, entitled "Surgical Stapler with Expandable Jaw," dated Sep. 24, 2015, 9 pgs.
The International Bureau of WIPO, International Preliminary Report on Patentability for International Application No. PCT/US2015/035379, entitled "Surgical Stapler with Circumferential Firing," dated Dec. 22, 2016, 14 pgs.
The International Bureau of WIPO, International Preliminary Report on Patentability for International Application No. PCT/US2015/050103, titled "Surgical Stapler With Self-Adjusting Staple Height," dated Mar. 30, 2017, 12 pgs.
European Patent Office, Partial European Search Report for European Application No. EP 14762896.0, entitled "Surgical Stapler with Expandable Jaw," dated Apr. 10, 2017, 6 pgs.
European Patent Office, Extended European Search Report for European Application No. EP 18186558.5, entitled "Surgical Stapler with Partial Pockets," dated Oct. 10, 2018, 9 pgs.

The International Bureau of WIPO, International Preliminary Report on Patentability, for International Application No. PCT/US2017/027142, entitled "Surgical Stapler Having Articulation Mechanism," dated Oct. 25, 2018, 12 pgs.
The International Bureau of WIPO, International Preliminary Report on Patentability, for International Application No. PCT/US2017/027213, entitled "Surgical Stapler Having Powered Handle," dated Oct. 25, 2018, 9 pgs.
The International Bureau of WIPO, International Preliminary Report on Patentability, for International Application No. PCT/US2017/027269, entitled "Reload Shaft Assembly for Surgical Stapler," dated Oct. 25, 2018, 12 pgs.
European Patent Office, Extended European Search Report for European Application No. EP 18189960.0, entitled "Surgical Stapler with Expandable Jaw," dated Dec. 13, 2018, 6 pgs.
European Patent Office, International Search Report and Written Opinion for International Application No. PCT/US2015/050103 titled "Surgical Stapler with Self-Adjusting Staple Height" dated Feb. 17, 2016, 18 pgs.
International Searching Authority/ EPO, Invitation to Pay Additional Fees and Communication Relating to the Results of the Partial International Search for PCT/US2019/019867, entitled "Surgical Stapler Having a Powered Handle," dated May 24, 2019, 19 pgs.
European Patent Office, The International Search Report and the Written Opinion of the International Searching Authority for International Application No. PCT/US2019/019867, entitled "Surgical Stapler Having a Powered Handle," dated Jul. 19, 2019, 24 pgs.
European Patent Office, Extended European Search Report for European Application No. EP 19150575.9, entitled "Surgical Stapler Having Actuation Mechanism with Rotatable Shaft," dated Aug. 21, 2019, 5 pgs.
European Patent Office, Extended European Search Report for European Application No. EP 19180055.6, entitled "Surgical Stapler with Circumferential Firing," dated Sep. 20, 2019, 8 pgs.
European Patent Office, The International Search Report and the Written Opinion of the International Searching Authority for International Application No. PCT/US2020/019938, entitled "Surgical Stapling Instrument Having a Two-Position Mechanism," dated Jun. 18, 2020, 16 pgs.
European Patent Office, Extended European Search Report for European Application No. EP 20157713.7, entitled "Surgical Stapler with Expandable Jaw," dated May 11, 2020, 6 pgs.
International Searching Authority/ EPO, Invitation to Pay Additional Fees for PCTUS2020/025496, entitled "Reload Cover for Surgical Stapling System," dated Jun. 18, 2019, 15 pgs.
European Patent Office, Extended European Search Report for European Application No. EP 20161294.2, entitled "Surgical Stapler with Self-Adjusting Staple Height," dated Jun. 22, 2020, 6 pgs.
European Patent Office, The International Search Report and the Written Opinion of the International Searching Authority for International Application No. PCT/US2020/025496, entitled "Reload Cover for Surgical Stapling System," dated Aug. 13, 2020, 20 pgs.
European Patent Office, The International Search Report and Written Opinion for International Application No. PCT/US2020/067540, dated May 3, 2021, entitled "Electrosurgical System with Tissue and Maximum Current Identification," 12 pages.
European Patent Office, Extended European Search Report for European Application No. EP 21162419.2, entitled "Surgical Stapler Having Articulation Mechanism," dated Jun. 22, 2021, 10 pgs.
The International Bureau of WIPO, International Preliminary Reporton Patentability, for International Application No. PCT/US2020/019938, entitled "Surgical Stapler Having a Two-Position Lockout Mechanism," dated Sep. 10, 2020, 10 pgs.
The International Bureau of WIPO, International Preliminary Report on Patentability, for International Application No. PCT/US2020/025496 entitled "Reload Cover for Surgical System," dated Oct. 14, 2021, 12 pgs.
European Patent Office, Extended European Search Report for European Application No. EP 21173771.3, entitled "Reload Shaft Assembly for Surgical Stapler," dated Aug. 27, 2021, 10 pgs.

* cited by examiner

SURGICAL STAPLER HAVING LOCKING ARTICULATION JOINT

CROSS REFERENCE TO RELATED APPLICATION

This application is a continuation of U.S. patent application Ser. No. 15/230,833, entitled "SURGICAL STAPLER HAVING LOCKING ARTICULATION JOINT," filed Aug. 8, 2016 which claims the benefit of U.S. Provisional Patent Application Ser. No. 62/201,995, entitled "SURGICAL STAPLER HAVING LOCKING ARTICULATION JOINT," filed Aug. 6, 2015. The above-referenced applications are incorporated by reference herein in their entireties.

BACKGROUND OF THE INVENTION

Field of the Invention

The present application relates generally to surgical occlusion instruments and, more particularly, to surgical staplers.

Description of the Related Art

Surgical staplers are used to approximate or clamp tissue and to staple the clamped tissue together. Laparoscopic surgical staplers can have a stapler jaw assembly disposed at a distal end of an elongate shaft. The stapler jaw assembly can be introduced to a surgical site through a trocar cannula or other surgical access port. It can be desirable to articulate the stapler jaw assembly relative to the elongate shaft to enhance access to the surgical site. Laparoscopic surgical staplers have had various mechanical and electro-mechanical articulation systems that can allow a user to control an articulated position of the jaw assembly at the distal end of the stapler from a control at the proximal end of the stapler. However, these mechanisms can undesirably add complexity to the handle assembly and jaw assembly of the staplers. With these complex mechanisms, surgical staplers can have increased manufacturing burdens, as well as potential sources for device failure and confusion for the user. Thus, reliable articulation of the jaw assembly of a surgical stapler stapling of clamped tissue without complex mechanisms is desired.

SUMMARY OF THE INVENTION

In certain embodiments, a surgical stapler is described. The surgical stapler comprises an elongate shaft, a jaw assembly, an articulation joint, and a handle assembly. The elongate shaft has a proximal end and a distal end with a longitudinal axis being defined between the proximal end and the distal end. The jaw assembly is positioned at the distal end of the elongate shaft. The jaw assembly comprises a first jaw; and a second jaw. The jaw assembly has an elongate configuration defining a jaw axis. The articulation joint couples the elongate shaft to the jaw assembly. The articulation joint has an unlatched configuration in which the jaw assembly is pivotable with respect to the elongate shaft upon application of an external force to the jaw assembly and a latched configuration in which the jaw assembly is pivotally secured with respect to the elongate shaft. The handle assembly is positioned at the proximal end of the elongate shaft. The handle assembly comprises an articulation latch lever. The articulation latch lever is movable between a proximal, latched position in which the articulation joint is in the latched configuration and a distal, unlatched position in which the articulation joint is in the unlatched configuration.

In certain embodiments, a surgical stapler is described. The surgical stapler comprises an elongate shaft, a jaw assembly, an articulation joint, and a handle assembly. The elongate shaft has a proximal end and a distal end and a longitudinal axis is defined between the proximal end and the distal end. The jaw assembly is positioned at the distal end of the elongate shaft. The jaw assembly comprises a first jaw and a second jaw. The jaw assembly has an elongate configuration defining a jaw axis. The articulation joint couples the elongate shaft to the jaw assembly. The articulation joint has an unlatched configuration in which the jaw assembly is pivotable with respect to the elongate shaft upon application of an external force to the jaw assembly and a latched configuration in which the jaw assembly is pivotally secured with respect to the elongate shaft. The articulation joint comprises a pivot pin and an alignment spring. The pivot pin pivotally couples the jaw assembly to the elongate shaft. The pivot pin has a wedge profile. The alignment spring spans the wedge profile of the pivot pin. The alignment spring biases the jaw axis into alignment with the longitudinal axis. The handle assembly is positioned at the proximal end of the elongate shaft.

In certain embodiments, a surgical stapler is described. The surgical stapler comprises an elongate shaft, a jaw assembly, and an articulation joint. The elongate shaft extends from a proximal end to a distal end along a longitudinal axis. The jaw assembly is positioned at the distal end of the elongate shaft. The jaw assembly comprises a first jaw and a second jaw. The jaw assembly has an elongate configuration defining a jaw axis. The articulation joint couples the elongate shaft to the jaw assembly. The articulation joint has an unlatched configuration in which the jaw assembly is pivotable with respect to the elongate shaft upon application of an external force to the jaw assembly and a latched configuration in which the jaw assembly is pivotally secured with respect to the elongate shaft. The articulation joint comprises a support member, a pivot member, and a latch member. The support member comprises a central pivot aperture and a plurality of latch recesses. The pivot member is pivotably coupled to the support member at the central pivot aperture. The latch member is slidable between a proximal position in engagement with one of the latch recesses corresponding to the latched configuration of the articulation joint and a distal position out of engagement with the plurality of latch recesses corresponding to the unlatched configuration of the articulation joint.

DETAILED DESCRIPTION OF THE INVENTION

Figure 1:
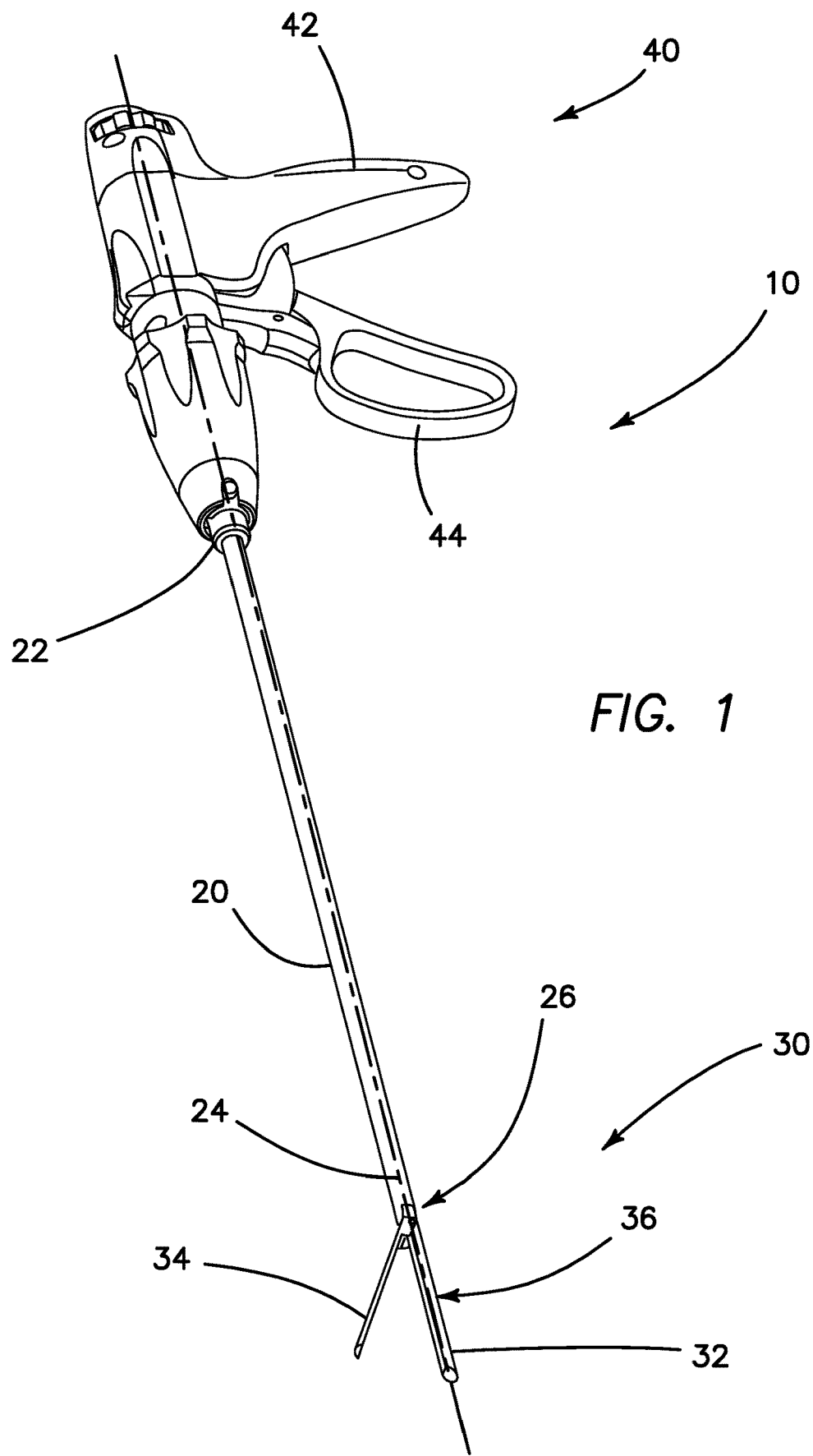
FIG. 1 is a perspective view of an embodiment of surgical stapling device with the jaws in an open configuration.

With reference to FIG. 1, an embodiment of surgical stapling device is illustrated. The illustrated embodiment of surgical stapler 10 comprises an elongate shaft 20, a jaw assembly 30, and a handle assembly 40. FIG. 1 illustrates the surgical stapler 10 with the jaw assembly 30 in an open configuration.

With continued reference to FIG. 1, the illustrated embodiment of surgical stapler 10 can be sized and configured for use in laparoscopic surgical procedures. For example, the elongate shaft 20 and jaw assembly 30 can be sized and configured to be introduced into a surgical field through an access port or trocar cannula. In some embodiments, the elongate shaft 20 and jaw assembly 30 can be sized and configured to be inserted through a trocar cannula having a relatively small working channel diameter, such as, for example, less than 8 mm. In other embodiments, elongate shaft 20 and jaw assembly 30 can be sized and configured to be inserted through a trocar cannula having a larger working channel diameter, such as, for example, 10 mm, 11 mm, 12 mm, or 15 mm. In other embodiments, it is contemplated that certain aspects of the surgical staplers described herein can be incorporated into a surgical stapling device for use in open surgical procedures.

With continued reference to FIG. 1, as illustrated, the elongate shaft 20 comprises a generally tubular member. The elongate shaft 20 extends from a proximal end 22 to a distal end 24. The elongate shaft 20 defines a central longitudinal axis, L. of the surgical stapler 10 extending between the proximal end 22 and the distal end 24.

With continued reference to FIG. 1, in the illustrated embodiment, the jaw assembly 30 is coupled to the elongate shaft 20 at the distal end 24 of the elongate shaft 20. An articulation joint 26 can join the jaw assembly 30 to the elongate shaft 20. The jaw assembly 30 comprises a first jaw 32 and a second jaw 34 pivotally coupled to the first jaw 32. In the illustrated embodiment, the first jaw 32 is fixed to the articulation joint 26 at the distal end 24 of elongate shaft 20 such that in an aligned orientation, it extends distally along the central longitudinal axis, L. The jaw assembly extends from a proximal end, which is coupled to the articulation joint 26 along a jaw axis to a distal end. The articulation joint 26 can allow the jaw assembly 30 to be positioned in an aligned orientation (FIG. 1) in which the jaw axis is aligned with the central longitudinal axis, or can allow the jaw assembly 30 to be selectively positioned in one of a plurality of articulated positions in which the jaw axis is transverse to the central longitudinal axis. In an initial configuration, the first jaw 32 includes a plurality of staples 36 disposed therein, such as within a reload assembly or cartridge.

With continued reference to FIG. 1, in the illustrated embodiment, the jaw assembly 30 can be actuated from an open configuration (FIG. 1) to a closed configuration to a stapling configuration by an actuation member or beam that is longitudinally slidable within the elongate shaft. In an initial position, the beam can be positioned at the distal end 24 of the elongate shaft 20. With the beam in the initial position, the second jaw 34 is pivoted away from the first jaw 32 such that the jaw assembly 30 is in the open configuration. The actuation beam engages the second jaw 34 upon translation of the actuation member or beam distally along the longitudinal axis L. Translation of the actuation beam distally from the initial position a first distance can actuate the jaw assembly from the open configuration to the closed configuration. With the jaw assembly 30 in the closed configuration, the actuation beam can be returned proximally the first distance to return the jaw assembly 30 to the open configuration. A distal end of the actuation beam can advance a staple slider configured to deploy staples from the first jaw 32 such that further translation of the actuation beam distally past the first distance deploys the plurality of staples 36 from the first jaw 32.

With continued reference to FIG. 1, in the illustrated embodiment, the handle assembly is coupled to the elongate shaft 20 at the proximal end 22 of the elongate shaft 20. As illustrated, the handle assembly 40 has a pistol grip configuration with a housing defining a stationary handle 42 and a movable handle 44 or trigger pivotably coupled to the stationary handle 42. It is contemplated that in other embodiments, surgical stapler devices including aspects described herein can have handle assemblies with other configuration such as, for example, scissors-grip configurations, or in-line configurations. The handle assembly 40 can include a mechanical or electromechanical actuation assembly that moves the actuation beam responsive to movement of the stationary handle 42 or trigger.

In some embodiments, the surgical stapler 10 can include the plurality of staples 36 positioned in a disposable cartridge while the handle assembly 40 is configured to be reused with multiple staple cartridges. In the illustrated embodiment, the elongate shaft 20 and jaw assembly 30 define a disposable cartridge that is removably couplable to the handle assembly 40. Accordingly, in the illustrated embodiment the handle assembly 40 includes a coupler 46 at the distal end thereof. The coupler 46 is adapted to engage the elongate shaft 20 of the surgical stapler 10. The coupler 46 can comprise a bayonet connection having an outer connector that can removably couple to handle assembly 42 the elongate shaft 20, and an inner connector that can removably couple the actuation shaft of the handle assembly 42 to the actuation member of the elongate shaft 20. Accordingly, the surgical stapler 10 can be configured such that the handle assembly 40 can be reused with multiple disposable cartridges during a surgical procedure. It is contemplated that in other embodiments, the handle assembly and some portion of the elongate shaft can be reusable while a remainder of the elongate shaft and the jaw assembly define a disposable cartridge. In certain other embodiments, the handle assembly and the elongate shaft can be reusable while the jaw assembly defines a disposable cartridge. In still other embodiments, a jaw insert housing a plurality of staples can define a disposable cartridge while the remainder of the surgical stapler is reusable with multiple disposable cartridges.

Figure 2:
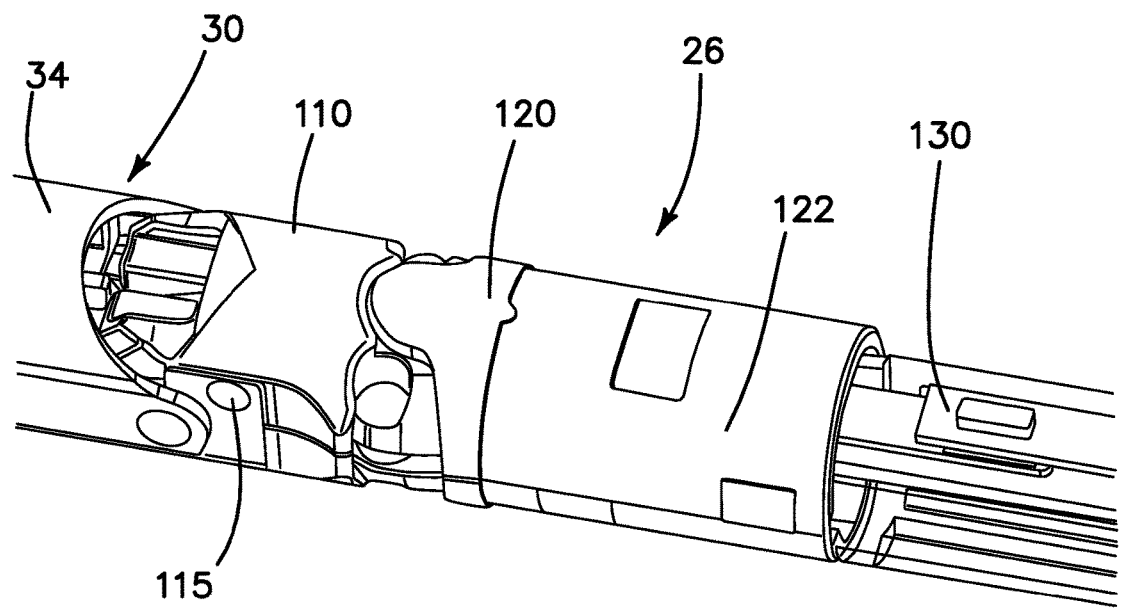
FIG. 2 is a perspective view of an embodiment of an articulation joint for a surgical stapler.
Figure 3:
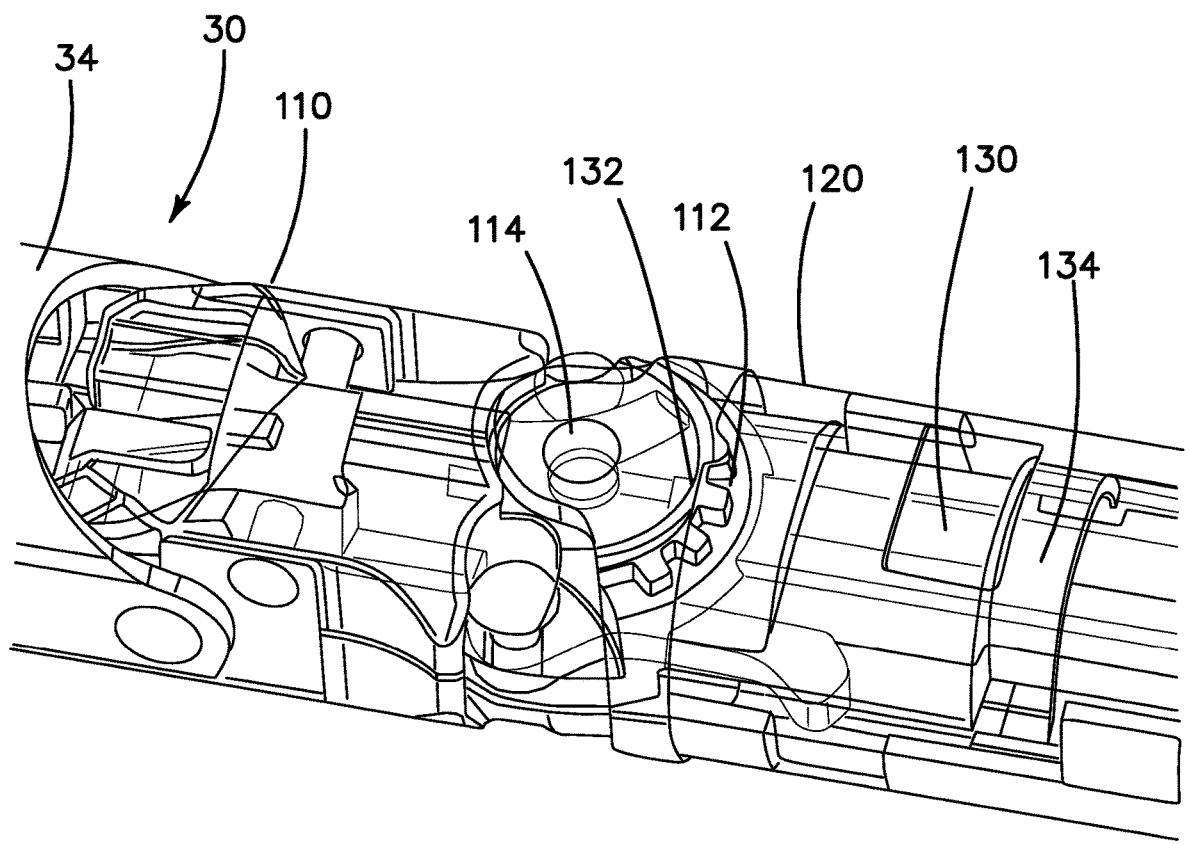
FIG. 3 is a perspective view of the articulation joint of FIG. 2 with portions of the a support member and pivot member depicted as transparent to illustrate a latch mechanism therein.

With reference to FIGS. 2-3, a perspective view of the articulation joint 26 is illustrated. The articulation joint can comprise a support member 110 pivotally coupled to a pivot member 120. The articulation joint can further comprise a latch member 130 to selectively latch and unlatch the articulation joint 26. The support member 110 can be coupled to the proximal end of the jaw assembly 30, and the pivot member 120 can be coupled to the distal end of the elongate shaft (not illustrated to enhance visualization of the articulation joint). In the illustrated embodiment, the support member 110 is coupled to the jaw assembly at a riveted or pinned connection 115 as further described herein. In some embodiments, the pivot member 120 can include a coupling sleeve 122 portion that can be slid into the distal end of the elongate shaft.

With reference to FIG. 3, the articulation joint 26 is illustrated with the support member 110 and pivot member 120 illustrated as translucent to enhance visualization of the articulation latching mechanism therein. The support member can comprise a pivot 114. In the illustrated embodiment, the pivot of the support member comprises an aperture formed therein in which a pin-like protrusion 124 extending radially inward from the pivot member 120 is positioned to allow relative pivotal movement of the support member 110 and pivot member 120 at the pivot 114. In other embodiments, the support member can comprise a pin-like protrusion formed therein and the pivot member can include a pivot aperture for receiving the protrusion. In still other embodiments, the support member and pivot member can each include a pivot aperture that are pivotally coupled to one another by a separate pin or rivet.

With continued reference to FIG. 3, the support member 110 further comprises a latch 112 at the proximal end thereof. The latch member 130 can extend distally past the proximal end of the support member 110 to selectively engage the latch 112 to pivotally fix the articulation joint 26 in a latched configuration. The latch member 130 extends longitudinally through the elongate shaft of the stapler from a proximal end to a distal end. The latch member 130 can comprise an elongate strip 134 extending through the elongate shaft 20. The latch member 130 further comprises a protrusion or latching tooth 132 extending from the distal end of the latch member 130.

The latch member 130 is longitudinally slidable with respect to the central longitudinal axis of the elongate shaft between a distal position and a proximal position. With the latch member 130 slid longitudinally distally to a distal position, the latching tooth 132 can be positioned distally of the latch 112 such that the articulation joint 26 is in an unlatched configuration. In the unlatched configuration, the jaw assembly can be pivoted with respect to the elongate shaft about the pivot 114 responsive to an external force on the jaw assembly 30. The external force can be applied by, for example, a surface of a surgical site or interaction with another surgical instrument such as the surgical access port or a laparoscopic tool. With the latch member 130 in the proximal position, the latching tooth 132 engages the latch 112 of the support member 110 to pivotally fix the jaw assembly with respect to the elongate shaft. The latch member can desirably be biased to the proximal position such that the articulation joint is biased to the latched configuration. For example, in some embodiments, a biasing member or spring positioned within the elongate shaft can engage the elongate strip 134 to bias the latch member 130 to the proximal position.

Figure 4:
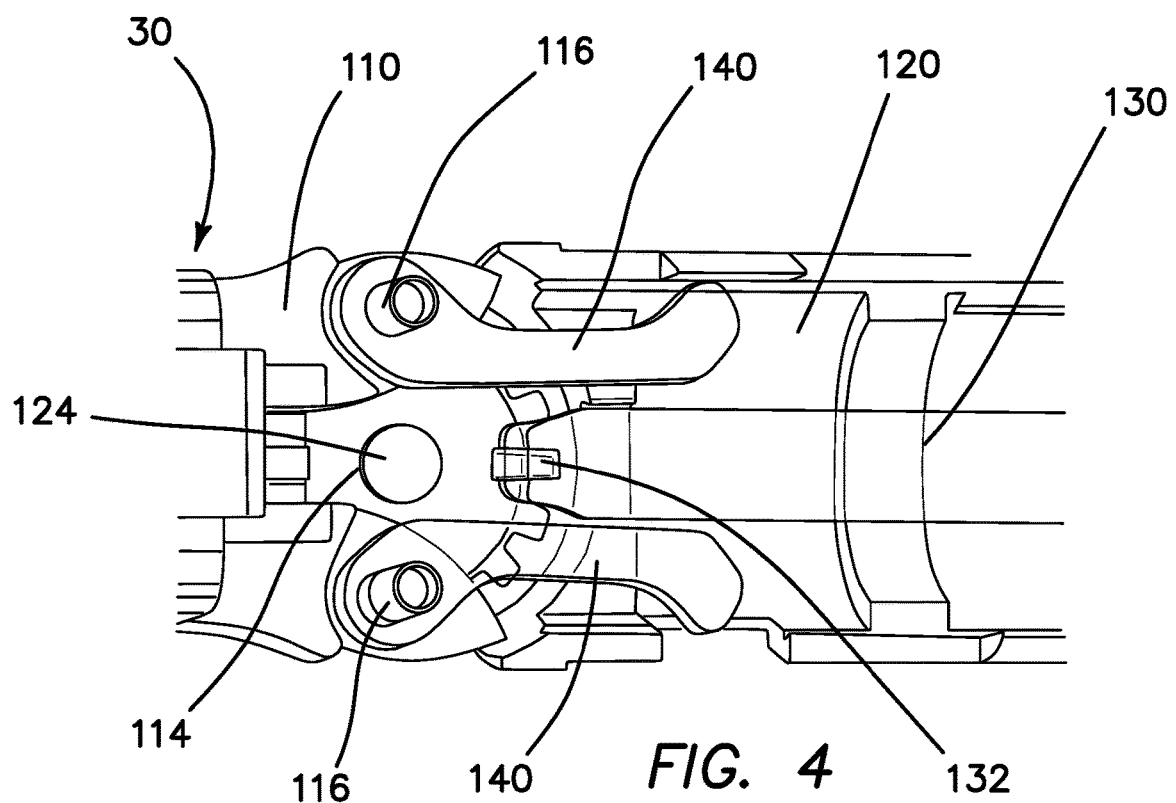
FIG. 4 is a cut away view of the articulation joint of FIG. 2 with the jaw assembly in an aligned orientation.
Figure 5:
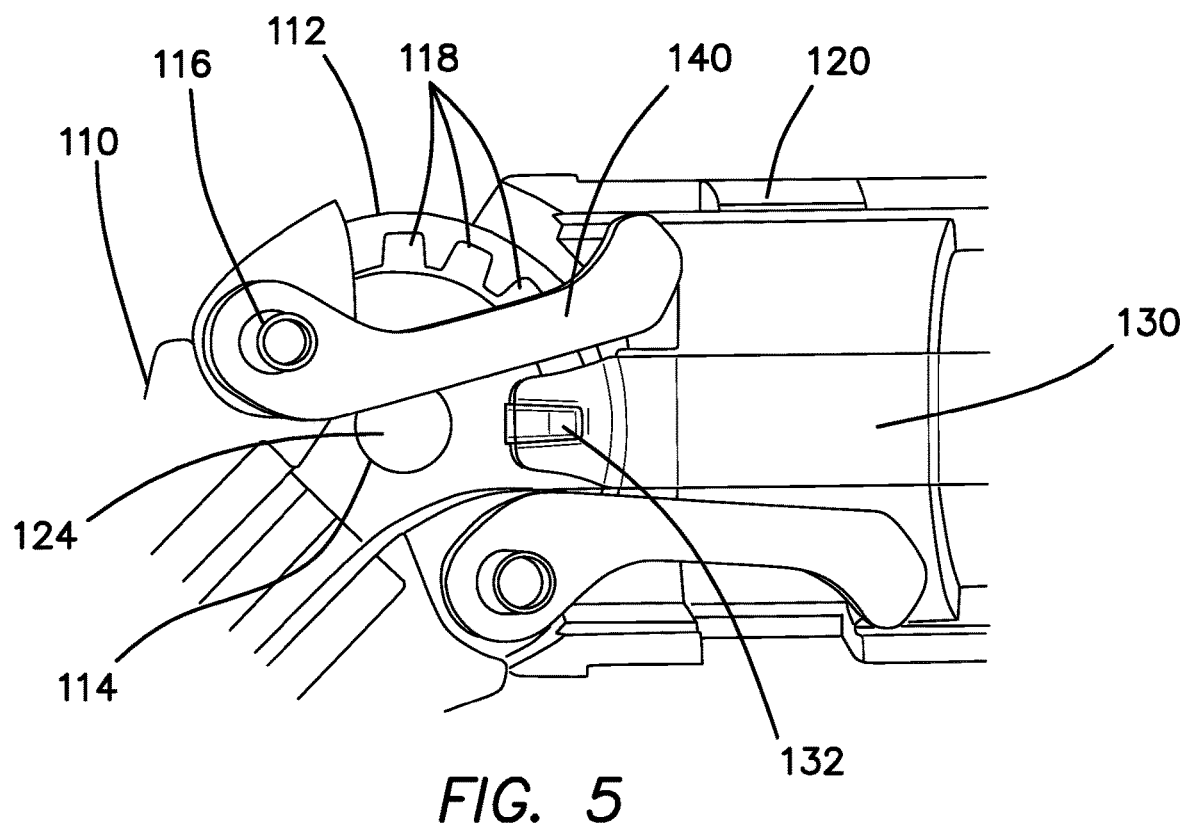
FIG. 5 is a cut away view of the articulation joint of FIG. 2 with the jaw assembly in an articulated orientation.

With reference to FIGS. 4 and 5, the latch mechanism of the articulation joint is illustrated in an aligned position (FIG. 4) and an articulated position (FIG. 5). In the illustrated embodiment, the latch 112 at the proximal end of the support member 110 comprises a plurality of latch recesses 118 that are arranged in a generally arc-shaped array proximal the pivot 114. The latch recesses 118 each comprise an open end at a distal end thereof. With the articulation joint in an unlatched configuration, as the jaw assembly and support member 110 coupled thereto are pivoted about the pivot 114 with respect to the elongate shaft and pivot member 120, one of the plurality of latch recesses 118 aligns with the tooth 132 of the latch member to define a corresponding latch position of the articulation joint. In the illustrated embodiment, the latch 112 comprises five latch recesses 118 such that the articulation joint is pivotable between an aligned position and four articulated positions in which the jaw axis is transverse to the central longitudinal axis. In other embodiments, the latch 112 can have more or fewer than five latch recesses to define a corresponding number of latch positions. Each of the latch recesses 118 can have a radiused or tapered 'lead in' to facilitate engagement of the tooth 132 of the latch member 130 with one of the plurality of latch recesses 118 in the event of slight misalignment between the latch recess 118 and the latch member 130.

With continued reference to FIGS. 4 and 5, the articulation joint can be configured to allow a flexible staple actuation or drive member to pass therethrough and minimize buckling of the flexible actuation member when the articulated joint is in an articulated position. For example, the support member can comprise a pair of support link pivots 116 laterally offset from the pivot 114 and a corresponding pair of support links 140 coupled to the support link pivots 116. Each support link of the pair of support links 140 can be pivotally coupled to a corresponding one of the support link pivots and extend generally proximally into the pivot member 120 towards the elongate shaft. The support links 140 define a channel therebetween in which the flexible actuation member can extend. As the articulation joint 26 is positioned in an articulated position (FIG. 5), the support links 140 pivot with respect to the support member 110 to maintain the channel for the flexible actuation member. Thus, the support links 140 can provide a substantially continuous channel wall to prevent the flexible actuation member from buckling or bowing at the articulation joint as the actuation member passes through the articulation joint.

Each of the support links 140 can be sized to extend between the support member 110 and the pivot member 120 over a full articulation range of the articulation joint. In the illustrated embodiment, each of the support links 140 include a curved first end pivotably coupled to one of the support link pivots 116, a curved second end opposite the first end, and a central span extending between the first end and the second end. The curved second ends can extend into sliding contact with the pivot member 120 to further support the flexible actuation member positioned in the channel between the central spans of the support links.

Figure 7:
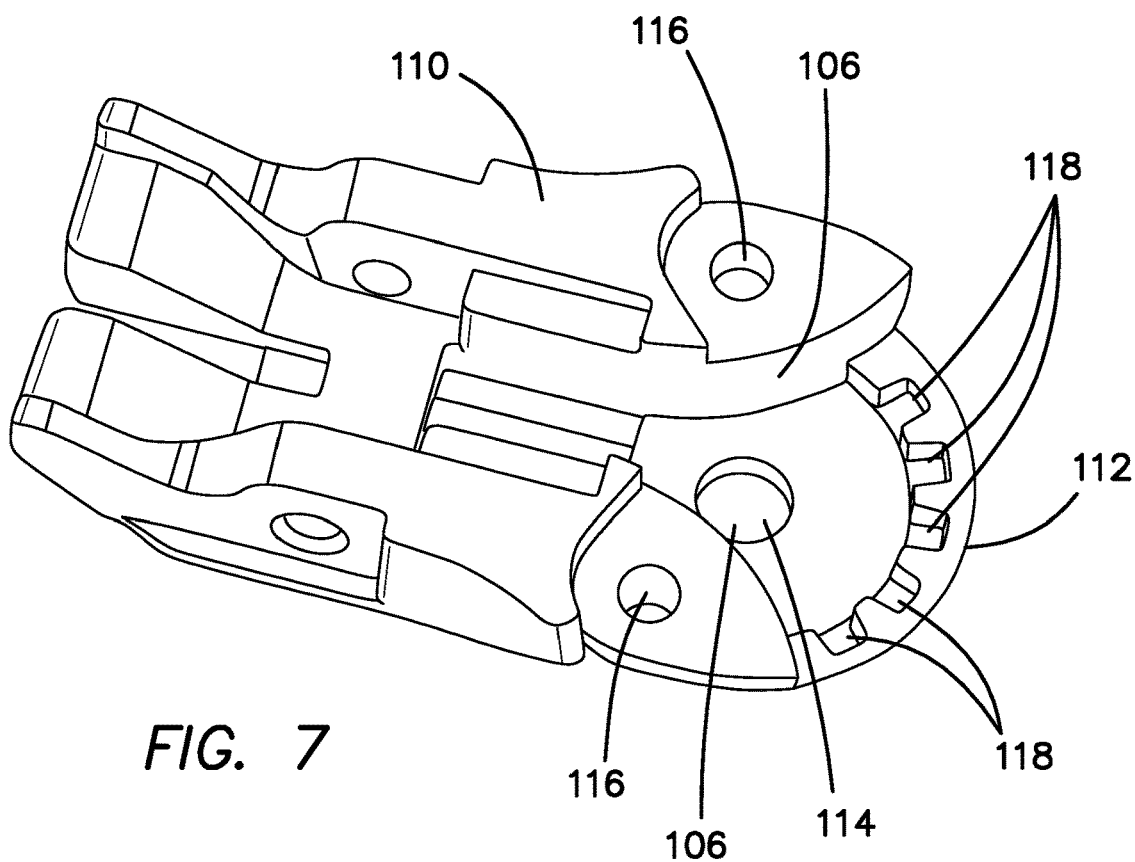
FIG. 7 is a perspective view of a support member of the articulation joint of FIG. 2.

With reference to FIG. 7, a perspective view of the support member 110 is illustrated. The latch 112 including latch recesses 118 are illustrated at the proximal end thereof. The pivot 114, comprising a pivot aperture, is illustrated at a central position of the support member. The pair of support link pivots 116 are positioned laterally offset from the pivot 114. In the illustrated embodiment, the support link pivots are each disposed on radiused sidewall surfaces 106 that facilitate a radiused bend for a flexible actuation member extending therethrough when the articulation joint is in an articulated position.

Figure 6:
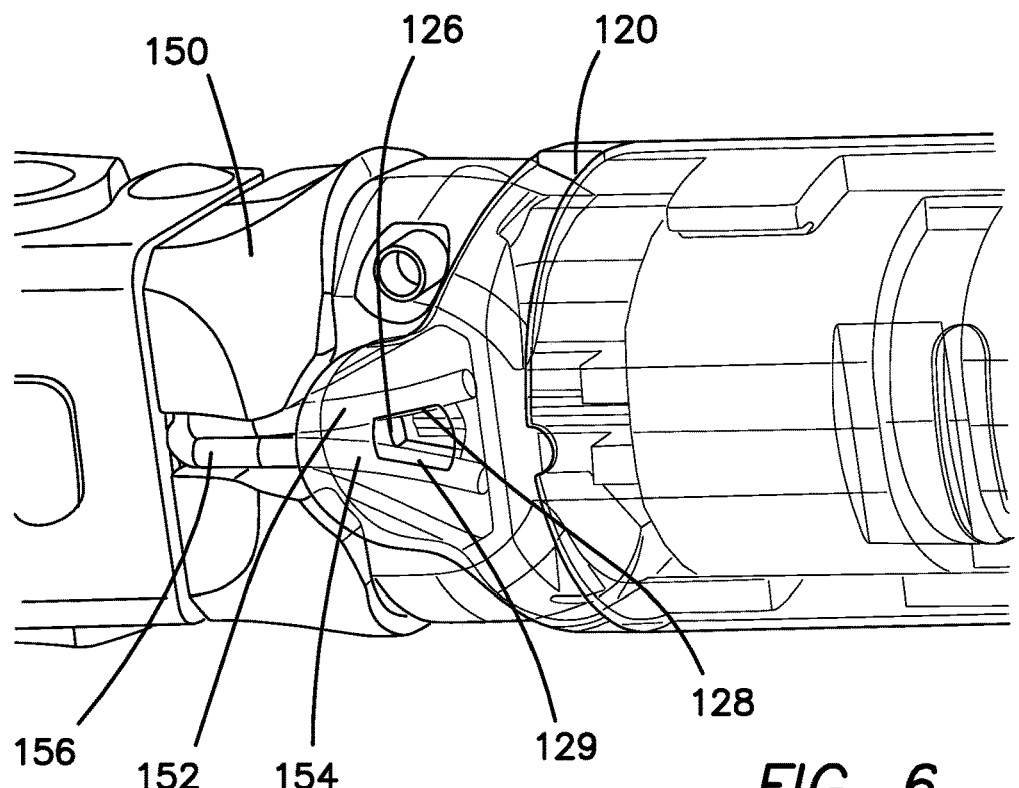
FIG. 6 is a perspective view of a lower surface of the articulation joint of FIG. 2 with portions of the lower housing depicted as transparent to illustrate the mechanism therein.

With reference to FIG. 6, a lower view of the articulation joint is illustrated. The pivot member 120 is illustrated as translucent, providing a cut away view to enhance visualization of an embodiment of alignment mechanism of the articulation mechanism. The alignment mechanism can be configured to bias the jaw axis into alignment with the central longitudinal axis of the elongate shaft. In the illustrated embodiment, the articulation mechanism comprises a lower support member 150 that can be coupled with the support member 110 and the jaw assembly. The lower support member 150 is pivotally coupled to the pivot member 120. In the illustrated embodiment, the pivot member 120 has a protruding pivot pin 126 having a wedge profile. The wedge profile is defined by a portion of the pivot pin 126 having a first substantially planar face 128 on a lateral edge thereof and a second substantially planar face 129 opposite the first substantially planar face. In the illustrated embodiment, the first and second substantially planar faces 128, 129 are transverse to one another. A spring 156 can span the pivot pin 126. The spring 156 can have a first leg 152 that is engageable with the first substantially planar surface 128 and a second leg 154 that is engageable with the second substantially planar surface 129. When the jaw assembly is misaligned with the elongate shaft, one leg of the spring engages the corresponding surface of the pivot pin 126 to bias the jaw assembly towards an aligned orientation.

Accordingly, in order to articulate the jaw assembly, a user first releases the latch mechanism to configure the articulation mechanism in an unlatched configuration. Then the user applies a force to the jaw assembly in a desired articulation direction. The applied force can be generated by bearing the jaw assembly against an anatomic feature in the surgical field or against another surgical instrument. In order to articulate the jaw assembly, the applied force overcomes the biasing force applied by the spring 156 of the alignment mechanism. With the stapler in the desired articulated position, the user can engage the latch mechanism to configure the articulation joint in the latched configuration. If it is desired to return the jaw assembly to an aligned configuration, such as, for example to remove the stapler from a surgical port, the user can release the latch mechanism and allow the bias of the alignment mechanism to return the jaw assembly to an aligned orientation.

Figure 8:
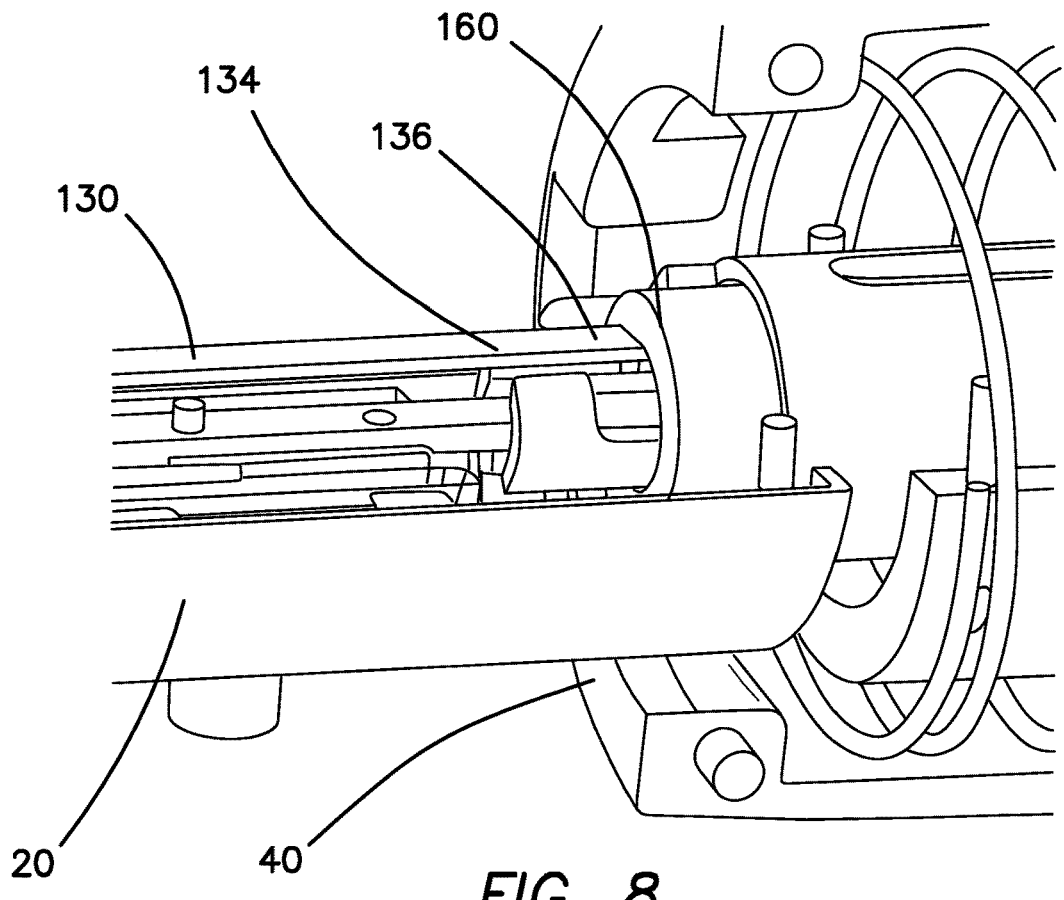
FIG. 8 is a partial cut-away view of a connection between an elongate shaft and a handle assembly of a surgical stapler.
Figure 9:
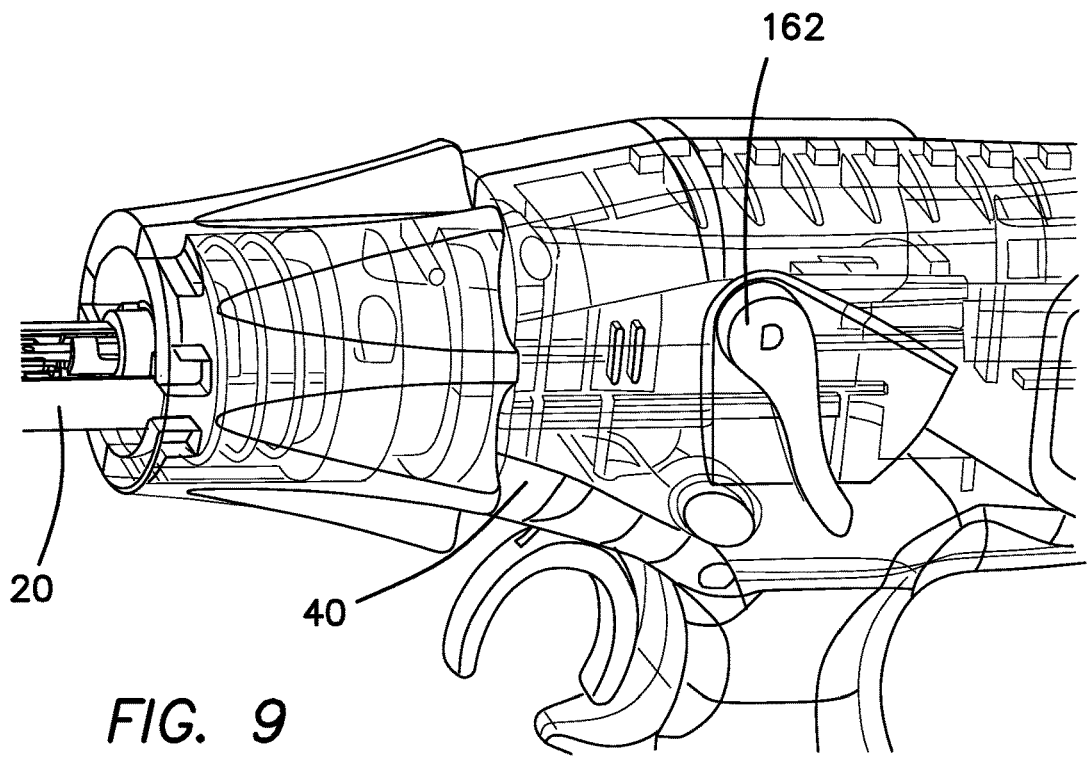
FIG. 9 is a perspective view of the handle assembly of FIG. 7 with the a handle housing depicted as transparent to illustrate the mechanism therein.
Figure 10:
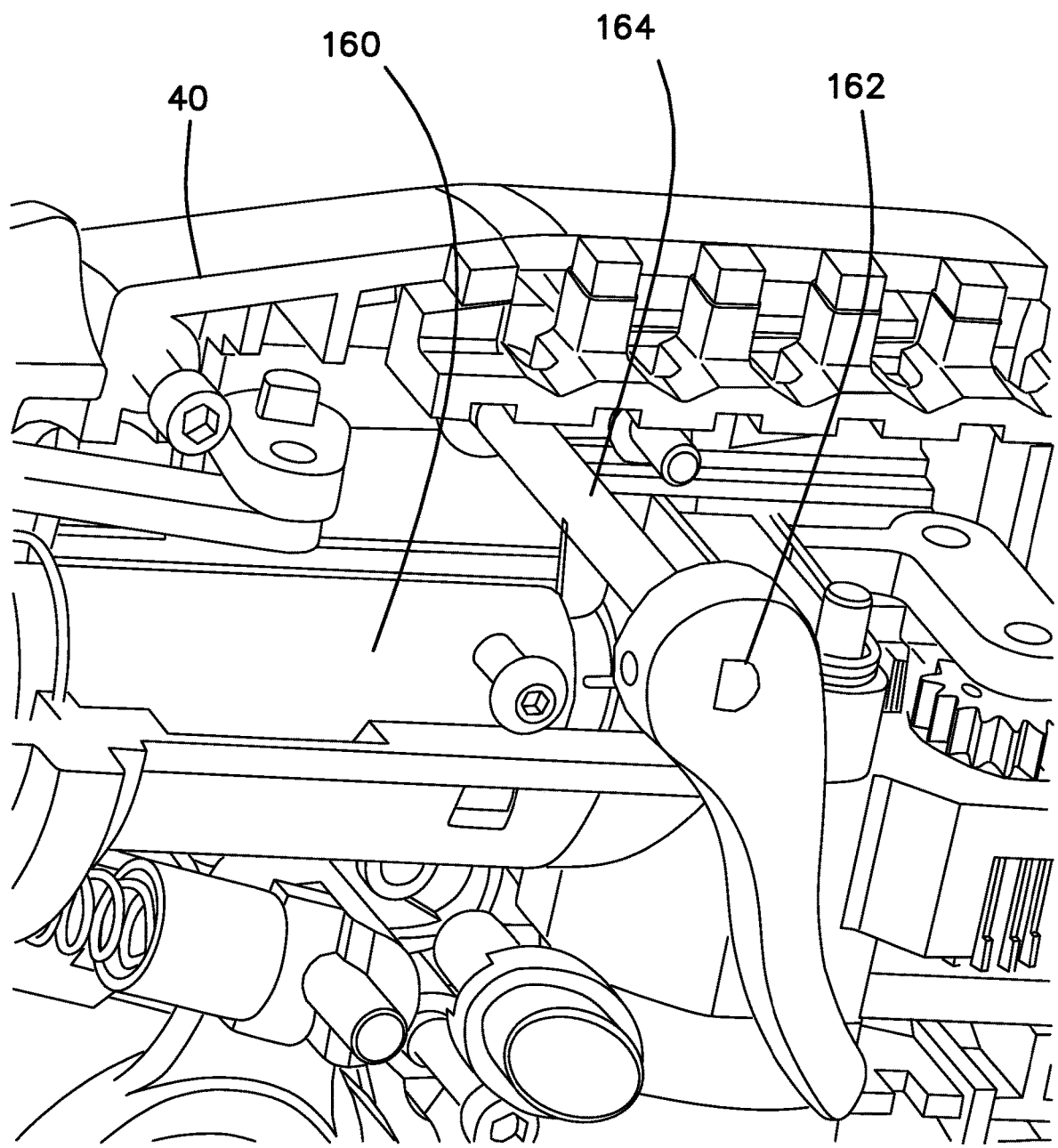
FIG. 10 is a cut away view of the handle assembly of FIG. 7.

With reference to FIGS. 8-10 an embodiment of latch release mechanism in the handle assembly 40 is illustrated. The latch release mechanism includes an articulation latch lever 162 in the handle assembly 40 for selectively controlling the articulation joint. FIG. 9 illustrates a thumb control articulation latch lever 162 positioned on a side of a handle assembly 40 to allow single-handed operation of the articulation joint. The handle assembly 40 is removably coupled to the elongate shaft 20. FIG. 8 provides a detailed cut away view of the handle assembly 40 to elongate shaft 20 connection. As illustrated, the elongate strip 134 of the latch member 130 extends through the elongate shaft 20 to the proximal end of the elongate shaft 20. Advantageously, since the latch member 130 is biased proximally and has a 'push-to-release' operation, a proximal end 136 of the elongate strip 134 merely needs to abut a longitudinally advanceable release member, which simplifies connection of the articulation joint to a lever mechanism on the handle assembly. Alternatively, a latch member with 'pull-to-release' operation could require a mating engagement, such as a bayonet connection, with a lever mechanism on the handle assembly.

With reference to FIGS. 8 and 10, operation of the articulation latch lever to push the latch member 130 is illustrated. As illustrated in FIG. 10, the articulation latch lever 162 extends from an end of an axle 164 such that movement of the latch lever 162 rotates the axle about a rotation axis thereof. A link couples the axle to a groove on an articulation sleeve 160. In the illustrated embodiment, the articulation sleeve 160 is a generally tubular member that extends distally to a distal end of the handle 40 (FIG. 8). When the elongate shaft 20 is coupled to the handle, the latch member 130 of the articulation joint abuts the articulation sleeve 160. In operation, when a user advances an end of the articulation latch lever 162 distally, the articulation sleeve 160 is correspondingly advanced distally and the abutting latch member 130 is pushed distally. The distal end of the latch member 130 is thus disengaged from a latch recess of the articulation joint to allow the jaw assembly to be pivoted responsive to a force external to the jaw assembly.

Advantageously, in the illustrated embodiment with 'push-to-release' interaction of the articulation sleeve 160 and latch member 130, the proximal end of the latch member 130 and distal end of the articulation sleeve 160 can be positioned in contacting or abutting engagement when the elongate shaft is coupled to the handle assembly. The proximal end of the latch member 130 can include a generally planar abutment surface that interfaces with a correspondingly generally planar release surface on the articulation sleeve 160. As illustrated, the articulation sleeve comprises an annular member such that the elongate shaft can be rotated about the longitudinal axis with continuous contact between the abutment surface of the latch member 130 and the release surface of the articulation sleeve. Thus, the elongate shaft can be rotatable about the longitudinal axis with respect to the handle assembly to facilitate desired positioning of the jaw assembly at a surgical site while maintaining the abutted connection of the latch release mechanism. Accordingly, such an arrangement can provide reliable latch release functionality for a handle assembly and removable elongate shaft without requiring relatively complex coupling, interfacing, or interlocking geometries for the articulation mechanism.

Although this application discloses certain preferred embodiments and examples, it will be understood by those skilled in the art that the present inventions extend beyond the specifically disclosed embodiments to other alternative embodiments and/or uses of the invention and obvious modifications and equivalents thereof. Further, the various features of these inventions can be used alone, or in combination with other features of these inventions other than as expressly described above. For example, it is contemplated that certain aspects of the articulation latch mechanisms and release mechanisms can be incorporated in stapling systems including manual or electrically powered staple deployment. Moreover it is contemplated that certain aspects of the articulation latch mechanisms and release mechanisms can be incorporated in stapling systems including manually selectable articulation mechanisms. Thus, it is intended that the scope of the present inventions herein disclosed should not be limited by the particular disclosed embodiments described above, but should be determined only by a fair reading of claims which follow.

What is claimed is:

1. A surgical instrument comprising:
   an elongate shaft having a proximal end and a distal end and defining a longitudinal axis between the proximal end and the distal end;
   a jaw assembly positioned at the distal end of the elongate shaft;
   an articulation joint coupling the elongate shaft to the jaw assembly, the articulation joint having an unlatched configuration in which the jaw assembly is pivotable with respect to the elongate shaft upon application of an external force to the jaw assembly and a latched configuration in which the jaw assembly is pivotally secured with respect to the elongate shaft; and a latch member comprising an elongate member having a proximal end and a distal end, the latch member longitudinally slidable within the elongate shaft with respect to the longitudinal axis of the elongate shaft between a proximal position in which the articulation joint is in the latched configuration and a distal position in which the articulation joint is in the unlatched configuration, and the distal end of the elongate member is positioned within the articulation joint in each of the proximal position and the distal position.

2. The surgical instrument of claim 1, wherein the articulation joint is biased to the latched configuration.

3. The surgical instrument of claim 2, wherein the elongate member is biased proximally to bias the articulation joint to the latched configuration.

4. The surgical instrument of claim 3, wherein the elongate shaft comprises a spring biasing the elongate member proximally.

5. The surgical instrument of claim 1, wherein the articulation joint comprises a support member having a central pivot defining a pivot axis of the articulation joint and a plurality of latch recesses.

6. The surgical instrument of claim 5, wherein with the latch member in the proximal position, the latch member engages one of the plurality of latch recesses.

7. The surgical instrument of claim 5, wherein the support member has a proximal end and a distal end, the plurality of latch recesses being positioned adjacent the proximal end, and wherein the latch member extends across the proximal end of the support member in both the proximal position and the distal position.

8. The surgical instrument of claim 5, wherein the plurality of latch recesses each comprise an open end at a distal end thereof and a closed end at a proximal end thereof and wherein the latch member engages the open end of one of the latch recesses with the articulation joint in the latched configuration.

9. The surgical instrument of claim 5, wherein the plurality of latch recesses is arranged proximal of the central pivot such that each latch recess defines a corresponding latched position of the articulation joint.

10. The surgical instrument of claim 5, wherein the latch member comprises a latching tooth at the distal end of the elongate member, the latching tooth configured to engage one of the plurality of latch recesses.

11. A surgical instrument comprising:
an elongate shaft having a proximal end and a distal end and defining a longitudinal axis between the proximal end and the distal end;
a jaw assembly positioned at the distal end of the elongate shaft, the jaw assembly defining a jaw axis;
an articulation joint coupling the elongate shaft to the jaw assembly, the articulation joint having an unlatched configuration in which the jaw assembly is pivotable with respect to the elongate shaft upon application of an external force to the jaw assembly and a latched configuration in which the jaw assembly is pivotally secured with respect to the elongate shaft, and the articulation joint comprising:
a pivot pin pivotally coupling the jaw assembly to the elongate shaft, the pivot pin having a wedge profile defined by a first substantially planar face on a lateral edge thereof and a second substantially planar face opposite the first substantially planar face; and
an alignment spring spanning the wedge profile of the pivot pin, the alignment spring biasing the jaw axis into alignment with the longitudinal axis, the alignment spring having a first leg abutting the first substantially planar face and a second leg abutting the second substantially planar face.

12. The surgical instrument of claim 11, wherein the articulation joint comprises:
a support member comprising:
a central pivot aperture;
a first support link pivot laterally offset from the central pivot aperture;
a second support link pivot laterally offset from the central pivot aperture opposite the first support link pivot; and
a plurality of latch recesses;
a latch member longitudinally slidable with respect to the longitudinal axis between a distal position in which the articulation joint is in the unlatched configuration and a proximal position in which the latch member engages one of the plurality of latch recesses such that the articulation joint is in the latched configuration.

13. The surgical instrument of claim 12, wherein the articulation joint further comprises:
a first support link extending from the first support link pivot proximally into the elongate shaft; and
a second support link extending from the second support link pivot proximally into the elongate shaft.

14. A surgical instrument comprising:
an elongate shaft extending from a proximal end to a distal end along a longitudinal axis;
a jaw assembly positioned at the distal end of the elongate shaft; and
an articulation joint coupling the elongate shaft to the jaw assembly, the articulation joint having an unlatched configuration in which the jaw assembly is pivotable with respect to the elongate shaft upon application of an external force to the jaw assembly and a latched configuration in which the jaw assembly is pivotally secured with respect to the elongate shaft, and the articulation joint comprising a plurality of latch recesses, each latch recess having an open end and a closed end proximal the open end; and
a latch member having a proximal end and a distal end, the latch member slidable between a proximal position in which the distal end of the latch member is positioned between the open end and the closed end of one of the latch recesses in engagement with the one of the latch recesses corresponding to the latched configuration of the articulation joint and a distal position distal of the open end of the one of the latch recesses and out of engagement with the plurality of latch recesses corresponding to the unlatched configuration of the articulation joint.

15. The surgical instrument of claim 14, wherein the latch member is biased to the proximal position.

16. The surgical instrument of claim 14, wherein the proximal end of the latch member is positioned at the proximal end of the elongate shaft.

17. The surgical instrument of claim 16, wherein the proximal end of the latch member comprises an abutment surface.

18. The surgical instrument of claim 17, further comprising a handle assembly removably couplable to the proximal end of the elongate shaft, wherein the handle assembly comprises a latch release mechanism positionable in contact with the abutment surface of the latch member when the handle assembly is coupled to the elongate shaft.

19. A surgical instrument comprising:
- an elongate shaft having a proximal end and a distal end and defining a longitudinal axis between the proximal end and the distal end;
- a jaw assembly positioned at the distal end of the elongate shaft, the jaw assembly defining a jaw axis;
- an articulation joint coupling the elongate shaft to the jaw assembly, the articulation joint having an unlatched configuration in which the jaw assembly is pivotable with respect to the elongate shaft upon application of an external force to the jaw assembly and a latched configuration in which the jaw assembly is pivotally secured with respect to the elongate shaft, and the articulation joint comprising:
  - a support member comprising:
    - a central pivot aperture;
    - a first support link pivot laterally offset from the central pivot aperture;
    - a second support link pivot laterally offset from the central pivot aperture opposite the first support link pivot; and
    - a plurality of latch recesses;
  - a latch member longitudinally slidable with respect to the longitudinal axis between a distal position in which the articulation joint is in the unlatched configuration and a proximal position in which the latch member engages one of the plurality of latch recesses such that the articulation joint is in the latched configuration;
  - a pivot pin pivotally coupling the jaw assembly to the elongate shaft, the pivot pin having a wedge profile; and
  - an alignment spring spanning the wedge profile of the pivot pin, the alignment spring biasing the jaw axis into alignment with the longitudinal axis.

20. The surgical instrument of claim 19, wherein the articulation joint further comprises:
- a first support link extending from the first support link pivot proximally into the elongate shaft; and
- a second support link extending from the second support link pivot proximally into the elongate shaft.

* * * * *